(12) United States Patent
O'Riordan et al.

(10) Patent No.: US 7,579,181 B2
(45) Date of Patent: Aug. 25, 2009

(54) PURIFICATION OF ADENOVIRUS AND AAV

(75) Inventors: Catherine E. O'Riordan, Jamaica Plain, MA (US); Amy L. (Ericson) Helgerson, Charlton, MA (US); Alan E. Smith, Dover, MA (US)

(73) Assignee: Genzyme Corporation, Cambridge, MA (US)

( * ) Notice: Subject to any disclaimer, the term of this patent is extended or adjusted under 35 U.S.C. 154(b) by 223 days.

(21) Appl. No.: 11/179,865

(22) Filed: Jul. 12, 2005

(65) Prior Publication Data

US 2005/0244942 A1 Nov. 3, 2005

Related U.S. Application Data

(63) Continuation of application No. 10/470,604, filed on Mar. 2, 2004, now Pat. No. 7,015,026, which is a continuation of application No. 09/604,349, filed on Jun. 27, 2000, now abandoned, which is a continuation of application No. 09/011,828, filed as application No. PCT/US96/13872 on Aug. 30, 1996, now Pat. No. 6,143,548.

(60) Provisional application No. 60/002,967, filed on Aug. 30, 1995.

(51) Int. Cl.
*C12N 7/02* (2006.01)
(52) U.S. Cl. .................................. 435/239
(58) Field of Classification Search ........... None
See application file for complete search history.

(56) References Cited

U.S. PATENT DOCUMENTS

| 4,505,817 A | 3/1985 | Blomback |
| 4,505,822 A | 3/1985 | Blomback |
| 4,587,018 A | 5/1986 | Blomback |
| 4,640,778 A | 2/1987 | Blomback |
| 5,521,082 A | 5/1996 | Lewis |
| 5,607,851 A | 3/1997 | Pellegrini |
| 5,719,049 A | 2/1998 | Pellegrini |
| 5,837,520 A | 11/1998 | Shabram |
| 6,194,191 B1 * | 2/2001 | Zhang et al. ............ 435/239 |
| 6,905,862 B2 * | 6/2005 | Blanche et al. ........... 435/239 |

FOREIGN PATENT DOCUMENTS

| CA | 2214837 | 12/2005 |
| DE | 1168015 | 4/1964 |
| DE | 1951800 | 4/1971 |
| EP | 0187894 | 7/1986 |
| JP | 58-155868 | 9/1983 |
| JP | 64-51080 | 2/1989 |
| JP | 7-177882 | 7/1995 |
| SU | 1364342 | 1/1988 |

OTHER PUBLICATIONS

Flotte et al., 1995, Gene Therapy 2:29-37.
Chiorini et al., 1995, Human Gene Therapy 6:1531-1541.
Fisher et al., 1996, J. Virol. 70:520-532.
Hughe et al., 1995, Human Gene Therapy 6:1403-1416.
Ivanov, A.E., et al., 1990, Bioorg. Khim. 16:1028-1039.
O'Neill, P.F. et al., "Virus Harvesting and Affinity-Based Liquid Chromatography", Bio/Technology 11:173-178, 1993.
Tamayose et al., 1996, Human Gene Therapy 7:507-513.
The Virus Experimentology General Remarks, revised 2nd Ed., Japan National Institute of Preventative Health alumnae association Eds, Maruzen Corp., p. 382, 1973.
Virology, Hisao Uetake Eds., Rikogakusha Co., Ltd. p. 17, 1992.
International Preliminary Examination Report of PCT/US96/13872.
International Search Report of PCT/US96/13872.
PCT Written Opinion of PCT/US96/13872.

* cited by examiner

Primary Examiner—Mary E Mosher

(57) ABSTRACT

The present invention relates to the purification of large scale quantities of active (infectious) adenovirus and AAV, especially for use in therapeutic applications. In particular, the invention provides improved methods for contacting such viruses with suitable chromatographic materials in a fashion such that any damage to the virus, particularly to surface components thereof, resulting from contact with such chromatographic materials is minimized or eliminated. The result is the ability to rapidly and efficiently purify commercial level quantities of active (infectious) virus suitable for use in therapeutic applications, e.g. gene transfer/therapy procedures.

22 Claims, 14 Drawing Sheets

CONTROL VIRUS (CsCl PURIFIED)

VIRUS PURIFIED USING A THREE
STEP CHROMATOGRAPHIC PROCESS

PURIFICATION OF ADENOVIRUS AND AAV

DESCRIPTION

The present application is a continuation of Ser. No. 10/470,604 filed on Mar. 2, 2004, which is a continuation of Ser. No. 09/604,349 filed on Jun. 27, 2000 which is a continuation of Ser. No. 09/011,828, filed Jun. 29, 1998, which is the U.S. national stage filing under 35 U.S.C. Section 371 of the application PCT/US96/13872, filed on Aug. 30, 1996, which is related to and claims the benefit of the filing date of prior U.S. Provisional Patent Application Ser. No. 60/002,967, filed Aug. 30, 1995, the text of which is incorporated herein by reference.

FIELD OF THE INVENTION

The present invention relates to the purification of large scale quantities of active (infectious) adenovirus and AAV, especially for use in therapeutic applications. In particular, the invention provides improved methods for 10 contacting such viruses with suitable chromatographic materials in a fashion such that any damage to the virus, particularly to surface components thereof, resulting from contact with such chromatographic materials is minimized or eliminated. The result is the ability to rapidly and 15 efficiently purify commercial level quantities of active (infectious) virus suitable for use in therapeutic applications, e.g. gene transfer/therapy procedures.

BACKGROUND OF THE INVENTION

Molecular therapy of disease often involves the administration of nucleic acid to the cells of interest in order to confer a therapeutic benefit. Most commonly, recombinant viruses are engineered which take advantage of the natural infectivity of viruses and their ability to transport heterologous nucleic acid (transgene) to a cell. Widespread use of such recombinant viral vectors depends on strategies for the design and production of such viruses.

Most attempts to use viral vectors for gene therapy have relied on retrovirus vectors, chiefly because of their ability to integrate into the cellular genome. However, the disadvantages of retroviral vectors are becoming increasingly clear, including their tropism for dividing cells only, the possibility of insertional mutagenesis upon integration into the cell genome, decreased expression of the transgene over time, rapid inactivation by serum complement, and the possibility of generation of replication-competent retroviruses (Jolly, D., *Cancer Gene Therapy* 1:51-64, 1994; Hodgson, C. P., Bio Technology 13:222-225, 1995).

Adenovirus is a nuclear DNA virus with a genome of about 36 kb, which has been well-characterized through studies in classical genetics and molecular biology (Horwitz, M. S., "Adenoviridae and Their Replication," in Virology, 2nd edition, Fields, B. N., et al., eds., Raven Press, New York, 1990). Adenovirus-based vectors offer several unique advantages for delivering a therapeutic transgene to a cell, including, inter alia, tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39-66, 1992; Jolly, D., *Cancer Gene Therapy* 1:51-64, 1994).

Adeno-associated virus (AAV) is a single-stranded non-pathogenic DNA virus which is capable of integrating into the genome of an infected cell. This feature of the virus life cycle has focused attention on the use of AAV as a gene therapy vehicle (creating a recombinant adeno-associated vector, rAAV) to deliver a gene of interest for gene therapy. The ability of AAV to insert a therapeutic gene into the cell genome facilitates persistent expression of the gene of interest and reduces the need for repeated dosing of a gene therapy vector.

Current methods for the purification of adenovirus and adeno-associated virus (AAV) involve the use of density gradient centrifugation, which does not easily allow for large scale production of virus stocks for therapeutic use. A further limitation to widespread use of AAV vectors is the general lack of any adequate purification methods which yield high titers of AAV, while removing contaminating adenovirus required for the propagation of AAV vector stocks.

Ion-exchange, affinity chromatography and gel filtration are widely used column chromatography tools in protein purification. Until recently, however, these methods have been inapplicable to purification of adenoviruses. Such techniques have resulted in damage to the viruses, thereby reducing their ability to bind and infect a target cell. Provisional U.S. patent application Ser. No. 60/002,967, filed Aug. 30, 1995, set forth parameters for purifying infectious adenovirus utilizing chromatographic fractionation techniques as described more fully herein. Recent studies have shown that column chromatography may be used in the purification of recombinant adenovirus (Huyghe et al., Human Gene Therapy 6:1403-1416, 1995).

Column chromatography, using other systems such as so-called "macroporous" resins, which comprise beads having pores therein, the average diameter of which is approximately the same as the diameter of adenovirus (diameter=about 80 nm, excluding the fibres and about 140 nm with the fibre molecules), have not resulted in the recovery of infectious adenovirus. The most likely reason for this is that the passage of adenovirus through such resins shears the fibres from the viral surface through intimate contact of the virus with the pores in the beads. The adenovirus fibre molecules, inter alia, are believed to be involved in the virus's ability to bind to and infect target cells. Thus, damage or loss of the fibre molecules (as well as other surface molecules) by such prior art column methods results in the recovery of inactive (non-infectious) virus.

As is well known in the art, AAV propagation requires the use of helper virus, such as adenovirus. The requirement for helper virus complicates purification of AAV. Current approaches to AAV purification involve lysing of AAV infected cells using repeated cycles of freeze-thawing followed by the use of density gradient centrifugation to fractionate the cell lysate in order to obtain infectious AAV, free of cellular contaminants and substantially free of helper virus (such as adenovirus) required for AAV propagation. (Flotte et al., Gene Therapy 2: 29-37, 1995; Chiorini et al., Human Gene Therapy 6: 1531-1541, 1995; Fisher et al., J. Virol. 70: 520-532, 1996). Standard purification techniques generally result in very low yields (0.3-5%) of active (infectious) virus. Moreover, because of the helper-virus requirement, it has been difficult to obtain AAV that is totally free of the helper (e.g. adenovirus).

SUMMARY OF THE INVENTION

The present invention is directed to methods for the purification of commercially useful quantities of infectious adenovirus and AAV, especially for therapeutic use.

The present invention avoids the problems associated with prior art methods of purifying infectious virus and relies on chromatographic fractionation techniques which provide for large scale separation of infectious adenovirus that are useful in gene transfer of therapeutic transgenes to a host. Thus, the present invention provides improved methods for contacting therapeutically useful viruses with suitable materials used in chromatographic fractionation techniques in a fashion and under conditions such that the viruses, especially surface components thereof believed required for infectivity, are not damaged by such contact.

Especially in regard to adenovirus purification, the invention encompasses several design considerations involved in these improved methodologies. These design considerations are related in that they accomplish a similar objective—minimizing or eliminating damage to the virus by contact with various chromatographic materials used in purification. In particular, the approaches are intended to obviate the effect of the openings or pores in such materials which are involved in the partitioning of biological molecules.

In one aspect of the invention, a "batch"-type technique may be used. In this aspect, the virus is mixed with a suitable chromatographic material rather than subjected to a "flow-through" procedure. It is believed that with this approach, the virus particles are less likely to enter the pores in the beads and suffer damage.

A second aspect of the invention involves using chromatographic materials in which the pore size of the support material is so small that the virus cannot enter the pores during chromatographic fractionation (e.g. in a column or membrane). The reduction in pore size of such chromatographic materials can be accomplished, e.g. by increased cross-linking of the support matrix. The reduction in pore size prevents the viruses from entering the openings in the beads where they can be damaged.

Alternatively, chromatographic materials may be used which contain structures, e.g. "tentacles," that prevent viruses from getting close to the pores in the matrix material. Again, this serves to prevent or minimize damage to the virus particles.

In a third aspect of the invention, chromatographic materials may be used wherein the matrix of the materials contains openings or pores that are very large in size, i.e. pores that have a diameter significantly larger than the diameter of the adenovirus particles. Thus, the virus can be partitioned through the pores in such chromatographic materials without being damaged.

Based on these design considerations, the purification methods of the present invention allow for the use of wide variety of commercially available chromatographic materials known to be useful in fractionating biological materials. Useful support matrices of such materials can include, inter alia, polymeric substances such as cellulose or silica gel type resins or membranes or cross-linked polysaccharides (e.g. agarose) or other resins. Also, the chromatographic materials can further comprise various functional or active groups attached to the matrices that are useful in separating biological molecules.

As such, the methods of the invention also exploit the use of affinity groups bound to the support matrices with which the viruses interact via various noncovalent mechanisms, and can subsequently be removed therefrom. Preferred approaches presented in the present invention exploit ion-exchange (especially anion-exchange) type interactions useful in chromatographic fractionation techniques. Other specific affinity groups can involve, inter alia, the use of heparin and virus-specific antibodies bound to the support matrix. Of consideration in the choice of affinity groups in virus purification via the present techniques is the avidity with which the virus interacts with the chosen affinity group and ease of its removal without damaging viral surface molecules involved in infectivity.

Commercial-scale production of relatively high molecular weight virus species (e.g. adenovirus and AAV) at high yields of active (infectious) virus is achieved with these methods.

DETAILED DESCRIPTION OF THE INVENTION

Figure 1:
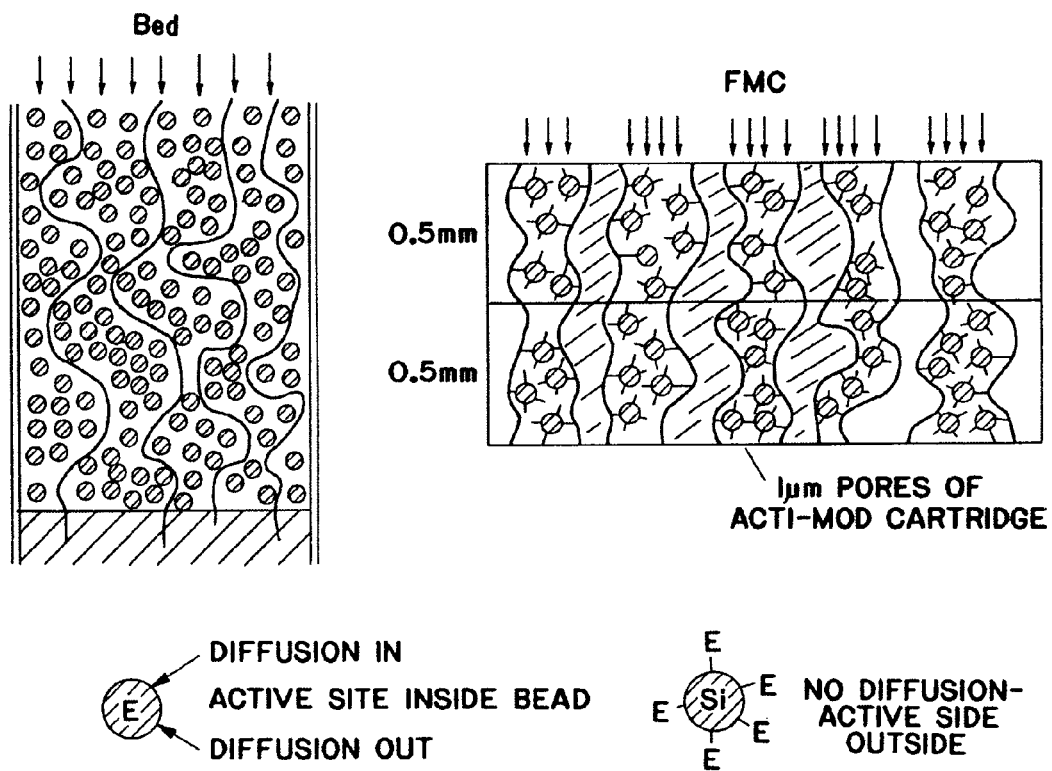
FIG. 1: Schematic diagram of Acti-Mod® Cartridge resin.

The present invention is directed to chromatographic fractionation methods adaptable for large scale for the purification of active (infectious) adenovirus and adeno-associated virus (AAV), especially for use in therapeutic applications, such as gene transfer, including gene therapy. The chromatography methods of the invention are intended to replace the current non-scaleable method of density-gradient ultracentrifugation of virus purification and allow for production of active (infectious) viruses on an industrial scale. The design strategies for purification of the two viruses are interrelated. As aforementioned, propagation of AAV requires the presence of helper-virus components, most commonly provided by adenovirus. The purification of AAV has been problematic because of adenoviral contamination.

The chromatographic fractionation techniques of the invention offer several advantages over prior virus purification procedures based solely upon centrifugation: the methods are rapid; the protocols are efficient, permitting separation of milligram quantities of virus in a single run; virus integrity is not compromised; and high yields of infectious virus are obtained.

Purification of Adenovirus

As aforementioned, prior attempts to adapt conventional chromatographic procedures and materials, such as those routinely used in the purification of proteins or other viruses, to the purification of adenovirus, have been unsuccessful. It is believed that in applying such procedures, insufficient care has been taken to protect the adenovirus from damage, and in particular, to macromolecular components thereof necessary for infectivity. Without being limited as to theory, it is recognized that particular adenoviral proteins, including most particularly the protein species known as "fibre" are involved in the binding of adenovirus to target cells during infection. Although numerous copies of such proteins may be found on each adenovirus, viral infectivity is relatively low for most cell types, and thus damage to even a small portion of, for example, the fiber molecules or other viral macromolecules can substantially prevent the establishment of successful infection. Maintaining high infectivity is therefore of considerable importance with respect to the commercial scale production of adenoviral vectors intended for therapeutic use, such as for gene therapy.

Accordingly, there are provided a wide variety of chromatography methods to take properly into account the fragile nature of adenovirus particles. As presently disclosed, a wide variety of conventional chromatographic materials including matrix or support materials, and the active (binding) groups routinely coupled thereto, are useful in the practice of the invention.

The methods described here in permit retrieval of purified adenoviral particles at high concentration in aqueous media without damage to adenoviral components. Similarly, the methods are suited to the preparation of milligram quantities of virus.

Adenovirus is isolated from virus-infected cells, for example, 293 cells. Cells may be infected at high multiplicity of infection (MOI) in order to optimize yield. Any method suitable for recovering virus from infected cells may be utilized. Preferred techniques for the recovery of virus from infected cells include freeze-thawing and the use of a microfluidiser. However, in order to make purification of viruses a scaleable process it is preferable to use procedures which lyse the virus infected cells without repeated freeze thawing and to remove cellular debris from the cell lysate without centrifugation. Optimal conditions for lysis of virus infected 293 cells for release of active virus may be achieved using a pressure cell, e.g. a Microfluidiser pressure cell (Microfluidics, Newton, Mass.). Ultrafiltration of the lysate using, for example, a Minitan system (Millipore, Bedford, Mass.), which comprises a High Resolution Tangential Flow System, can be used to further concentrate the virus fraction prior to chromatographic fraction techniques.

The adenovirus-containing lysate so obtained may then be subjected to the chromatographic fractionation techniques of the invention. In regard to adenovirus purification, the invention encompasses several design considerations involved in these improved methodologies. These design considerations are related in that they accomplish a similar objective—minimizing or eliminating damage to the virus by contact with various chromatographic materials used in purification. In particular, the approaches are intended to obviate the effect of the openings or pores in such materials which are involved in the partitioning of biological molecules.

In one aspect of the invention, a "batch"-type technique may be used. In this aspect, the virus is mixed with a suitable chromatographic material rather than subjected to a "flow-through" procedure. It is believed that with this approach, the virus particles are less likely to enter the pores in the beads where they can become damaged.

A second aspect of the invention involves using chromatographic materials in which the pore size of the support material is smaller than that of the virus particles so that the virus cannot enter the pores during chromatographic fractionation (e.g., in a column or membrane). The reduction in pore size of such chromatographic materials can be accomplished, e.g. by increased cross-linking of the support matrix. The reduction in pore size prevents the viruses from entering the openings in the beads where they can be damaged.

Alternatively, chromatographic materials may be used which contain structures, e.g. "tentacles," that prevent viruses from getting close to the pores in the matrix material. Again, this serves to prevent or minimize damage to the virus particles.

In a third aspect of the invention, chromatographic materials may be used wherein the matrix of the materials contains openings or pores that are very large in size, i.e., pores that have a diameter significantly larger than the diameter of the adenovirus particles. Thus, the virus can be partitioned through the pores in such chromatographic materials without being damaged.

Based on these design considerations, the purification methods of the present invention allow for the use of wide variety of commercially available chromatographic materials known to be useful in fractionating biological materials. Useful support matrices of such materials can include, inter alia, polymeric substances such as cellulose or silica gel type resins or membranes or cross-linked polysaccharides (e.g. agarose) or other resins. Also, the chromatographic materials can further comprise various functional or active groups attached to the matrices that are useful in separating biological molecules.

As such, the methods of the invention also exploit the use of affinity groups bound to the support matrices with which the viruses interact via various non-covalent mechanisms, and can subsequently be removed therefrom. Preferred approaches presented in the present invention exploit ion-exchange (especially anion-exchange) type interactions useful in chromatographic fractionation techniques. Other specific affinity groups can involve, inter alia the use of heparin and virus-specific antibodies bound to the support matrix. Of consideration in the choice of affinity groups in virus purification via the present techniques is the avidity with which the virus interacts with the chosen affinity group and ease of its removal without damaging viral surface molecules involved in infectivity.

The following types of chromatographic materials are suitable for the batch-type chromatographic methods discussed above.

The teachings of the present disclosure also make possible the use of other commercially available chromatographic materials, if only in batch form. Although not a preferred embodiment of the invention, once it is understood that adenovirus can be damaged by contacting such chromatographic materials, purification procedures can be redesigned to minimize damage to the virus. To the extent that many polymer materials contain pores which can damage any contacting adenovirus, such damage can be limited by minimizing, for example, column pressure, thereby limiting entry of adenovirus into matrix pores. In the simplest example thereof, the purification step is simply conducted in batch form. Polymer materials useful according to this aspect of the invention include the products Heparin Sepharose High Performance, of Pharmacia; macroporous hydroxyapatite such as Macro-Prep Ceramic Hydroxyapatite, Bio-Rad, Richmond, Calif.; and cellufine sulfate from Amicon.

Chromatography materials comprise polymers having sufficient matrix crosslinking such that interaction of adenovirus with any pore spaces thereof is minimized, wherein also are present any of a number of binding groups (including, for example, ion exchange groups or heparins) having affinity for the adenovirus. Representative heparinized polymers useful in the practice of the invention include those having about 6% more of crosslinking, such as Heparin Superflow Plus® (or Sterogene), a 6% crosslinked heparin agarose. Such an agarose matrix has an exclusion limit of about 6 million daltons which is expected to be much lower than that of a 4% crosslinked product, such as Heparin Agarose (Sigma Chemical Co.). In one experiment, recovery of adenovirus in infective form was substantially improved when the 6% rather than the 4% product was used. Additional polymers containing heparin groups that are useful in the practice of the invention include Heparin Sepharose® CL6B (Pharmacia).

Once the advantages of carefully controlled crosslinking are understood, it is apparent that those skilled in the art could substitute any number of polymer materials composed of any number of recognized matrix materials and binding groups such that the adenovirus is not damaged by contact therewith.

As to the second design consideration provided, representative chromatographic materials contain functional groups that interact effectively with adenovirus but which have a design that minimizes access of the virus to any pore spaces thereof (such as about 0.1 micron), which can damage the virus, and in particular, the fiber protein thereof.

Likewise, so-called tentacled polymers containing core regions to which are attached polymerized chains of varying lengths, and to which may be attached further functional groups; for example, Fractogel Tentacle Ion 25 Exchange Media available from E. Merck, Wakefield, R.I. These chromatographic materials are described as having an insoluble matrix copolymerized from oligoethyleneglycol, glycidylmethacrylate, and penta-erythrold-imethacrylate, to which are grafted polymerized chains of acrylamide derivatives, ending in ion exchanging groups such as DEAE, or quaternary aminoethyl, quaternary ammonimum, DMAE, TMAE, and the like, or, for example, $SO_3$- or carboxyl. It is within the practice of the invention to utilize similar "tentacled" materials.

Preferred, chromatographic materials regarding the third design comprise matrices having pores of at least about 0.1 μm (the size of an adenovirus), but preferably at least about 1 μm.

Such materials can be cellulose membrane or silica membrane cartridges characterized by high substrate specificity for target protomers, negligible binding of non-specific proteins, and a pore size (~1.2 μm) which is sufficient for purification of the largest known spheroidal viruses. The cartridge design, which consists of a stack of low-binding cellulose or silica membrane filters, is suited to high flow rates, while the large pore size (1.2 μm) of the cartridges eliminates the diffusion associated with beaded gel resins packed in columns.

For example, the ACTI-MOD® (American International, Natick, Mass.) cartridges consist of sheets of microporous silica/PVC. These silica sheets have a large surface area with numerous uniform pores (See FIG. 1, panel A). The pores are lined with silica to which different active side chains may be attached, e.g. DEAE or heparin structural units. During chromatography, the movement of virus through the highly porous silica/PVC sheets of ACTI-MOD® (or through the openings in similarly effective MemSep® (Millipore, Bedford, Mass.) cartridges) permits direct contact of the virions with the activated silica surface (FIG. 1, panel B). Such contact permits appropriate partitioning while, at the same time, avoiding adverse interaction of the virions with pores in the beads of the resin that are approximately the same size, or slightly smaller, than the size of the encapsulated virions themselves that occurs with the use of traditional beaded gel-type resins. Such adverse interaction may involve damage to virion surface components, including, for example, fibre protein, thereby reducing the ability of the virion to successfully infect target cells.

Additional polymer products which are useful in the practice of the invention are those containing pores which are large enough not to damage the virion and include, inter a spiral preparative chromatography modules, such as the CycloSep™ module (American International Chemical Inc., Natick, Mass.). The CycloSep™ spiral purification column has a matrix comprising a microporous plastic sheet (MPS®), with an integral rib design available in various spacing configurations. The matrix is wound into a spiral and is coated with silica. The resultant hydrophilic surface can be derivatized with various affinity ligands such as heparin, or those used in ion-exchange chromatography, such as DEAE and carboxymethyl.

Anion-exchange chromatography may be performed utilizing various functional moieties known in the art for anion-exchange techniques, including, but not limited to, DEAE, (diethyl aminoethyl), QAE (quaternary aminoethyl), and Q (quaternary ammonium). These functional moieties may be attached to any suitable resin useful in the present invention, including the cellulose and silica resins described herein. For example, DEAE may be attached to various resins, including cellulose resins, in columns such as DEAE-MemSep® (Millipore, Bedford, Mass.) Sartobind™ membrane absorbers (Sartorius, Edgewood, N.J.) and silica resins such as ACTI-MOD™, (American International Chemical, Natick, Mass.).

Cation-exchange chromatography also may be used for adenovirus purification, including, but not limited to, the use of such columns as SP MemSep® (Millipore, Bedford, Mass.), CM MemSep® (Millipore, Bedford, Mass.), Fractogel® $SO_3$-(EM Separation Technology, Gibbstown, N.J.)and Macroprep S® (BioRad, Melville, N.Y.), as well as heparin-based resins. Heparin ACTI-MOD® Cartridge (American International Chemical Inc., Natick, Mass.), and POROS® Perfusion chromatography media (Boehringer Mannheim) represent additional examples of this embodiment of the invention.

Other affinity ligands which may be used to purify adenovirus include anti-adenovirus antibodies attached to suitable resins as provided herein as well as others known to those skilled in the art.

Preferably, purification of adenovirus includes the following steps: pressure lysis of 293 cells infected with adenovirus in the presence of a detergent such as Tween-80 and recovery of virus in the lysate; clarification of lysate by passage through a 3 µm glass fiber filter and an 0.8 µm cellulose acetate filter; heparin chromatography using an ACTI-MOD® silica cartridge where adenovirus is recovered in the flow-through fraction; and DEAE-ion exchange chromatography using a MemSep® cartridge. Bound adenovirus is eluted from the DEAE-resin using 500-700 mM NaCl in a suitable buffer; followed by gel filtration (size exclusion) chromatography of the DEAE-eluate, where adenovirus is recovered in the void volume of the column eluate.

Gel filtration chromatography using, for example, resins such as Superdex® (Pharmacia, Piscataway, N.J.) to purify can be used to recover active adenovirus away from any contamination process. Such resins have a very small pore size (exclusion limit 2 million daltons) which results in the adenovirus being completely excluded from the beads of the resin and eluting in the void volume of the column. The partitioning functions in a similar fashion to a protein desalting column.

Adenovirus purification may be determined by assaying for viral proteins, using, for example, Western blotting or SDS-PAGE analysis. The identification of adenoviral DNA may be used as an indicator of virus recovery, using, for example, slot blot analysis, Southern blotting, or restriction enzyme analysis of viral DNA. Purification is evidenced by the predominance of viral proteins or nucleic acid in an assayed sample.

The identification of adenovirus particles may also be used to assay virus purification, using, for example, the spectrophotometric absorbance at 260 nm of a purified fraction, or the observance of virus particle by, for example, electron microscopy.

The recovery of infectious adenovirus may be determined by infection of a suitable host cell line (e.g., 293 cells) with a chromatographed sample. Infectious adenovirus may be dentified and titrated by plaque assays. Alternatively, infected cells may be stained for the abundant adenoviral hexon protein. Such staining may be performed by fixing the cells with acetone: methanol seven days after infection, and staining with a polyclonal FITC-labeled anti-hexon antibody (Chemicon, Temecula, Calif.). The 10 activity of a purified fraction may be determined by the comparison of infectivity before and after chromatography.

The use of other columns in the methods of the invention is within the scope of the invention directed to purification of adenovirus.

Since, as discussed above, AAV propagation requires helper adenovirus, which can purify with and contaminate AAV preparations, AAV purification takes advantage of chromatographic materials which damage adenovirus (e.g., through contact with the pores of such materials) in the purification of AAV. Thus, AAV purification uses chromatographic materials that are not preferred for adenovirus purification. For example, such materials can include the so-called "macroporous" resins discussed above, whose pore size is approximately that of adenovirus. In general, it is advantageous to select matrices with pore sizes that would damage adenovirus leading to its inactivation during purification.

The present invention also relates to methods for the separation of AAV from adenoviral and cellular proteins in the cell lysate, using column chromatography. The advantage of column chromatography over current non-scaleable methods of density-gradient ultracentrifugation is that large quantities of AAV can be produced. Another advantage of using column chromatography for the purification of AAV is that it effectively removes contaminating adenovirus which is used routinely as a helper virus in the production of AAV.

Purification of AAV

The initial lysis of AAV-infected cells can be accomplished via methods that chemically or enzymatically treat rather than physically manipulate the cells in order to release infectious virions. Such methods include the use of nucleases (such as benzonase®; DNAse) to enzymati-tally degrade host cell, non-encapsulated or incomplete adenoviral DNA. Proteases, such as trypsin, can be used to enzymatically degrade host cell, adenoviral or free AAV proteins. Detergents, surfactants and other chemical agents known in the art can also be used alone or in conjunction with enzymatic treatment.

AAV-infected cells can be further lysed by application to a pressure cell, such as a Microfluidiser pressure cell, wherein the intensified pumping system employs an accelerated suction stroke and a long slow pressure stroke to create a pressure profile of briefly interrupted constant pressure. This pressure is then used to lyse the AAV-infected cells, while gently retaining maximal activity of the AAV. A further advantage of the use of such pressure techniques for lysis is that such methods can be applied to scaled up cell culture conditions, including propagating cells on microcarriers. Alternatively, a French Pressure Cell (Baxter, Deerfield, Ill.), Manton Goulin Homgeniser (Baxter, Deerfield, Ill.) or Dynomill can be used. The resulting lysate can then be clarified by filtration through glass fiber filters or cellulose acetate filters. Alternatives include Millexe Durapore (Millipore, Bedford, Mass.) and Gelman Science Tufflyne filters (Gelman Science, Ann Arbor, Mich.). Filter sizes which may be used include 0.8 µm and 0.45 µm. If vacuum filtration is not used, glass wool also may be employed to clarify the lysate.

Suitable column chromatography methods to fractionate infected cell lysates for large-scale purification of AAV include the use of sulfated resins, such as Sterogene-S (Sulfated Hi Flow) (Sterogene, Carlsbad, Calif.), Spherilose-S (Isco, Lincoln, Nebr.), Cellufine® sulfate (Amicon, Beverly, Mass.). Such sulfated resins are capable of removing contaminating adenovirus from AAV using elution buffers containing about 400-500 mM, preferably about 475 mM NaCl.

DEAE containing resins used in AAV purification, include, but are not limited to, Puresyn DEAE (Puresyn, Malvern, Pa.), EM Merck Tentacle DEAE (Merk, Whitehouse Station, N.J.), Sterogene Superflow Plus DEAE (Sterogene, Carlsbad, Calif.), macroporous DEAE resins (Biorad, Melville, N.Y.), DEAE ACTI-MOD® (American International, Natick, Mass.), DEAE MemSep® (Millipore, Bedford, Mass.), all of which are capable of removing contaminating adenovirus.

Em Merck Tentacle DEAE is an ion exchange media consisting of a matrix copolymerized from oligoethyleneglycol, glycidymethacrylate and pentaerythroid to which are grafted polymerized chains of acrylamide derivatives approximately 15-50 units in length. Sterogene Superflow Plus® DEAE consists of a 6% cross-linked agarose to which is attached DEAE reactive groups. Macroporous DEAE resins are rigid hydrophilic supports with pore sizes of 80-100 nm, where the DEAE reactive groups are attached to the hydrophilic support. DEAE Acti-Mod® cartridge consists of sheets of microporous silica/PVC. These silica sheets have a large surface area with numerous uniform pores. The pores are lined with silica to which may be attached active side chains such as DEAE. This type of macroporous structure has pores of about 12,000 Å, or 1.2 µm, in width. In the DEAE MemSep® resin, the DEAE groups are covalently linked to the polymer matrix cellulose. A suitable elution buffer for the recovery of AAV from such resins comprises 200 mM NaCl in a phosphate buffer, pH 7.5.

Purification of AAV also utilizes hydroxyapatite resins, including the ceramic hydroxyapatite resins from Biorad (Melville, N.Y.). The recovery of AAV from such hydroxyapatite resins utilizes elution with a 100-135 mM phosphate buffer (pH 6.4, 10-400 mM phosphate gradient. The column is first washed with 30 mM phosphate and AAV elutes around 135 mM phosphate).

In a particular aspect of the invention, chromatography on cellulose or silica membrane resins is employed in conjunction with the use of macroporous resins in for effective large-scale purification of AAV. Examples of macroporous resins include the BioRad macroporous series (Melville, N.Y.) or the DEAE-Thruput (6% cross-linked agarose) (Sterogene, Carlsbad, Calif.). Silica or cellulose membrane resins include the DEAE-MemSep™ 1010 HP (Millipore), the ACTI-MOD® cartridge, or the CycloSep™ (American Chemical International) spiral purification column. Previous studies with macroporous resins showed them not to be very useful for the purification of adenovirus because the 80 nm pore size of the beads excludes and damages adenovirus particles having a diameter of 140 nm. However, this size limitation is an advantage for AAV purification, because these resins can remove contaminating adenovirus from AAV preparations based on the different sizes of the virion particles. It is well within the skill of those in the art to select macroporous resins for their ability to separate AAV from adenovirus based on discriminating pore size of the resins.

In a particular embodiment of the invention, pressure lysis of AAV-infected cells in the presence of detergent yields a cell lysate which is clarified by filtration. The lysate is then applied to a series of columns in order to separate AAV from cellular proteins and contaminating adenovirus. A preferred series of column separations includes the use of ceramic hydroxyapatite, DUE ion-exchange, Cellufine® sulfate, and zinc chelate chromatography. The AAV may be recovered from the columns as follows: hydroxyapatite (at 100-135 mM phosphate, pH 6.4); DEAE-ion exchange (at 200 mM salt in a phosphate buffer, pH 7.5); Cellufine® sulfate (at 425 mM salt in phosphate-buffered saline, pH 7.5) and in the flow-through from the zinc chelate column (Hepes buffer, pH 7.5).

A particularly preferred embodiment for purification of AAV includes the following steps: pressure lysis of AAV-infected 293 cells also infected with adenovirus in the presence of Tween-80 and trypsin, and recovery of virus in the lysate; clarification of lysate via filtration through an 0.45 μm or 0.8 μm cellulose acetate filter; ceramic hydroxyapatite chromatography (CHA), where bound AAV is eluted from the resin in 100-135 mM phosphate, pH 6.4; DEAE ion-exchange chromatography of the CHA eluate using a Mem-Sep® cartridge, where bound AAV is eluted from the resin in 200 mM salt (phosphate buffer, pH 7.5); Cellufine® sulfate chromatography of the DEAE-eluate, where bound AAV is eluted from the resin in 425 mM salt (phosphate-buffered saline, pH 7.5); and, optionally, zinc chelate chromatography where AAV is recovered in the flow through fraction (Hepes buffer, pH 7.5).

AAV may also be separated from adenovirus using Superdex® 200 resin (Pharmacia, Piscataway, N.J.), which separates AAV from low molecular weight contaminants, and where AAV is recovered in the void volume.

The methods described here permit retrieval of purified AAV particles at high concentration in aqueous media without centrifugal pelleting. Similarly the methods are suited to the preparation of milligram quantities of virus without the use of density centrifugation.

The use of other columns is also within the scope of the invention which is directed to the use of column chromatography in large scale purification of AAV.

In order to assess the integrity of a purification protocol, one skilled in the art can use any number of assays to determine whether AAV virus is recovered and whether cellular proteins and contaminating helper virus (such as adenovirus) have been removed. AAV recovery and purification can be monitored by determininq the levels of AAV DNA or AAV proteins in recovered fractions from the various chromatography steps, or from the titer of infectious virus.

The level of AAV DNA may be determined using a slot blot apparatus which detects immobilized DNA using an AAV specific probe. The number of viral particles can be determined with the use of a standard curve generated from samples of known particle number. Where recombinant AAV contains a marker gene, such as β-galactosidase, the amount of recovered virus can be determined by an appropriate assay for the marker gene product (e.g., X-gal) or by an assay that detects DNA copies of the gene (e.g., PCR).

Alternatively, the presence of virus may be determined from the level of AAV protein contained in recovered fractions. Viral proteins may be assayed by Western blotting, immunoprecipitation, Coomassie-stained SDS-PAGE gels, or any other methods for protein characterization and quantitation known to those skilled in the art. When an SDS-PAGE gel is stained with Coomassie Blue, the presence of other non-AAV proteins may be determined as an index of the concentration of the AAV fraction.

Purity of the isolated virus fraction is determined by SDS-PAGE analysis of proteins in the fraction, followed by Coomassie staining and densitometry. With respect to the AAV viral proteins, VP3 usually accounts for about 80% of the viral protein, while VP1 and VP2 together account for about 20% of total viral protein. Purity is assessed by the absence of heterologous proteins in assayed sample.

The purification methods of the invention may be applied to naturally occurring or recombinant viruses.

The practice of the invention employs conventional techniques of molecular biology, protein analysis and microbiology which are within the skill of the art. Such techniques are explained fully in, e.g., *Current Protocols in Molecular Biology*, Ausubel et al., eds., John Wiley & Sons, New York, 1995, which is incorporated herein by reference.

The invention is illustrated with reference to the following examples.

EXAMPLE 1

Extraction of Adenovirus from 293 Cells

A. Extraction of Adenovirus from Cells

The human embryonal cell line (293) was used to propagate adenovirus. Virus-infected cells were incubated until the cell monolayer exhibited extensive cytopathic effects (CPE). Usual infection time was 48-60 hours. The cells were harvested into phosphate-buffered saline (PBS) and collected by centrifugation at 1000×g. Cell pellets were frozen at −80° C. for further use or were resuspended in PBS containing 0.1% Tween-80, 10% glycerol, 2 mM $MgCl_2$ and 50 μM $ZnCl_2$. Following resuspension the cells were lysed using a Microfluidiser (Model HC5000, Microfluidics, Newton, Mass.) at 1000 psi and the lysate was incubated with benzonase (2500 units benzonase®/$10^8$ cells) for 1 hour at room temperature.

To remove cellular debris, the lysate was clarified by passing it through glass wool (without vacuum) or by vacuum filtration through 3.0 µm glass fiber filters (MicroFiltration Systems #C300A090C, Sierra Court-Dublin, Calif.). This was followed by filtration using an 0.8 µm cellulose acetate filter (MicroFiltration Systems 25 #CD80A090C, Sierra Court-Dublin, Calif.). Following clarification the lysate was either directly chromatographed or subjected to a further filtration step using a Minitan ultrafiltration system (Millipore, #XX42MT060, Bedford, Mass.) prior to chromatography.

B. Ultrafiltration

Lysate from 293 cells infected with adenovirus (prepared as discussed above) was passed through a Minitan Ultrafiltration System (Millipore #XX42MT060, Bedford, Mass.) at flow rates varying from 300-400 ml/min in the following buffer: phosphate buffered saline (PBS), 0.05% Tween-80, 10% glycerol, 50 µM $ZnCl_2$. To measure recovery of infectious units following ultrafiltration the retentate was assayed for adenovirus infectivity using the virus titer assay while recovery of protein in the retentate was measured using a BCA assay (Pierce Chemical Co. #23220, Rockford, Ill.).

Results

Table 1 provides a comparison between recovery of active adenovirus using both microfluidiser pressure lysis and freeze-thawing as methods of lysis for adenovirus infected cells. Using the microfluidiser and detergent-containing buffers, there was a 96% recovery of active virus with pressure lysis compared to lysis by freeze thawing. Thus, the microfluidiser provides an alternative effective lysis procedure, which has the advantage of allowing larger volumes of cells to be processed at one time. Also, methods to scale up cell culture conditions, including growing cells on microcarriers, are possible since the microfluidiser can effectively lyse cells attached to microcarriers. Lysis of the cells occurred in the presence of the nuclease Benzonase®, which degrades host cell, nonencapsulated or incomplete adenoviral nucleic acids.

Following lysis of the cells, the resulting lysate was clarified to remove cellular debris by filtration through glass wool or alternatively by using vacuum filtration through a 3.0 µm glass fiber filter (MicroFiltration Systems #300A090C, Sierra Court-Dublin, Calif.). A further filtration step using a 0.8 pm cellulose acetate filter (MicroFiltration Systems) was then carried out. Typically, 84% of active adenovirus was recovered in the final clarified lysate, while only 43% of total cell lysate protein was recovered.

Ultrafiltration was then used to further purify the clarified cell lysate prior to column chromatography. The molecular size of adenovirus is $150 \times 10^6$ daltons, while the molecular size of the majority of host cell contaminating proteins is expected to be lower. A Minitan® ultrafiltration system from Millipore (molecular weight cut-off membrane of 300 kDa) was used. Table 2 shows that the maximum recovery of infectious adenovirus units was achieved when the flow rate through the membrane was 200 ml/min and the buffer contained glycerol and trypsin. Under these conditions 100% of adenovirus activity was achieved while 55% of host cell proteins was removed. Spinner cultures of 293 cells (grown on microcarriers) and infected with adenovirus were used in these studies. Therefore, effective cell lysis and release of active adenovirus from 293 cells grown on microcarriers is possible using the Microfluidiser® pressure cell.

TABLE 1

Comparison of different methods for lysis of 293 cells infected with adenovirus

| | I.U. Total | % Activity recovered |
|---|---|---|
| Freeze Thaw (3×) | $4.3 \times 10^{11}$ | 100 |
| Microfluidiser | $4.1 \times 10^{11}$ | 96 |

TABLE 2

Ultrafiltration of Adenoviral Cell Lysates Using a Minitan System (Millipore)

| | Flow Rate (ml/min) | | |
|---|---|---|---|
| | 400 | 300 | 200 |
| I.U. before ultrafiltration ($\times 10^{10}$) | 6.4 | 33.44 | 3.2 |
| I.U. after ultrafiltration ($\times 10^{10}$) | 2.42 | 11.73 | 3.2 |
| % Adenovirus activity recovered | 38 | 70 | 100 |
| % Total protein remaining | 70 | 57.5 | 52 |

EXAMPLE 2

Chromatographic Purification of Adenovirus

Column resins were tested for their separation characteristics using a Pharmacia FPLC.

Methods

1. DEAE Chromatography

A. Adenovirus

A DEAE MemSep® 1010 HP (Millipore) column (5 ml) was equilibrated with phosphate buffered saline (PBS) (1.5 mM $KH_2PO_4$, 150 mM NaCl, 5 mM $Na_2HPO_4$ pH 7.5) containing 10% glycerol, 0.05% Tween-80, and 50 µM ZnCl2. Clarified lysate from 293 cells infected with adenovirus as prepared in Example 1 was applied at a flow rate of 5 ml/min to the pre-equilibrated column (in PBS, 10% glycerol, 0.05% Tween-80, 2 mM $MgCl_2$, 50 µM $ZnCl_2$). The column was washed with 10 mM $Na_2 HPO_4$, 100 mM NaCl, 100 mM KCl, and a linear gradient (100 mM–1 M) of KCl and NaCl in 10 mM $Na_2 HPO_4$ pH 7.5, 10% glycerol, 0.05% Tween-80 and 50 µM $ZnCl_2$ was applied to the resin at a flow rate of 5 ml/min. Bound proteins were eluted from the resin and collected in 5 ml fractions. Each fraction was monitored for a) adenoviral DNA and b) adenoviral proteins (as described below). Fractions which were positive for both adenoviral DNA and protein were assayed further for activity using the virus titre assay.

B. AAV

Cell lysates from 293 cells infected with adeno-associated virus AAV were also chromatographed using DEAE 25 MemSep® chromatography as above. However, the buffer used to lyse the cells and equilibrate the column was 10 mM sodium phosphate, pH 7.5, containing 50 mM NaCl and 1% NP-40. Bound proteins were eluted from the resin using a salt gradient as described above for adenovirus purification. Fractions collected from the resin were assayed for AAV DNA using a slot blot assay and AAV proteins by immunoblotting using an antibody (Catalog 03-65158, of American Research Products, Belmont, Mass.) against the three capsid proteins of AAV, VP1, VP2 and VP3.

2. Gel Filtration Chromatography

A. Adenovirus

Gel filtration chromatography was then performed using a Superdex® 200 HR 26/60 column (Pharmacia) equilibrated with PBS, 10% glycerol, 2 mM $MgCl_2$, 50 µM $ZnCl_2$, and 0.05% Tween-80. Fractions eluted from the DEAE resin which showed the presence of both adenoviral proteins and DNA were pooled and concentrated using a stir cell (Amicon) to a volume of 15 ml. The sample was applied to the Superdex® resin at a flow rate of 1 ml/min and 1.5 ml fractions were collected during elution. Fractions were assayed for adenoviral DNA and proteins as described below.

B. AAV

Adenovirus purified by the cesium chloride method (described below) was applied directly to the Superdexm resin following the final cesium chloride density centrifugation. This was to reduce the concentration of cesium chloride in the sample which normally was removed by dialysis.

In some experiments gel filtration chromatography of whole cell lysates of AAV was performed using a Superdex® 200 HR 26/60 prior to chromatography on a DEAE column.

Additional polymeric materials useful according to this aspect of the invention include cross-linked cellulose polymers such as Sulfate Spherilose (ISCO).

Results

Figure 2:
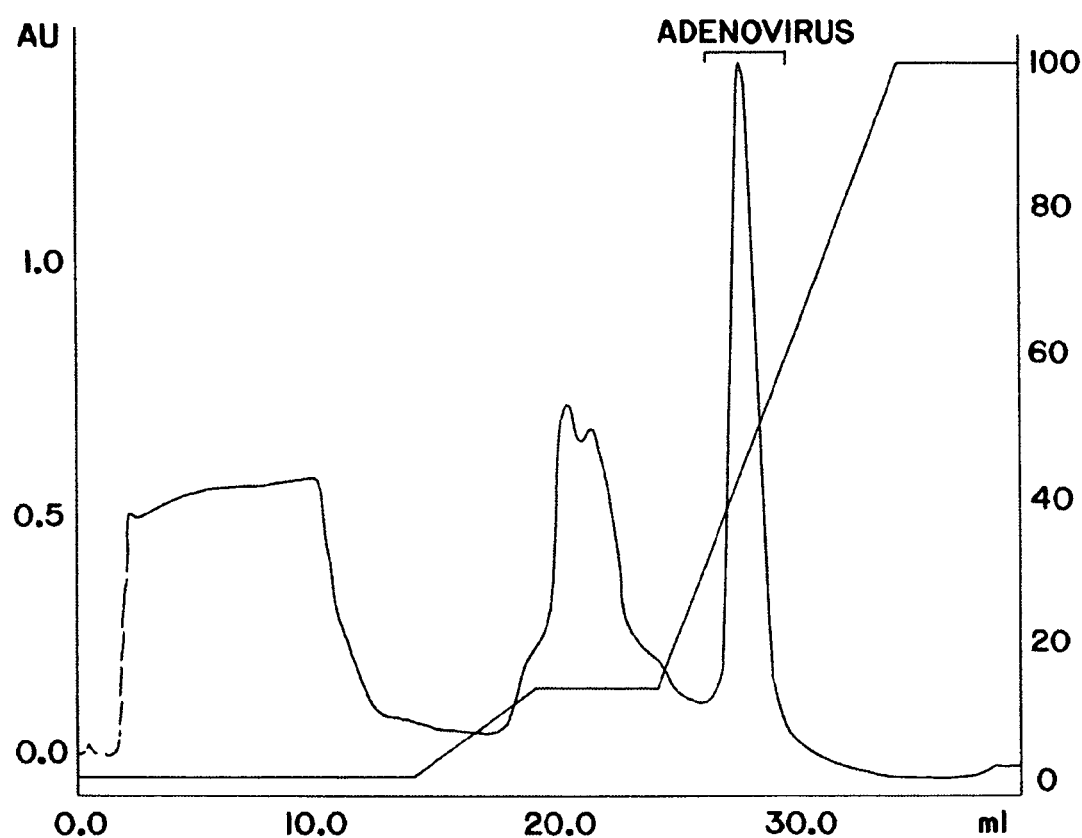
FIG. 2: Chromatogram showing elution profile of adenovirus from DEAE-MemSep® resin. Elution peak for adenovirus is labelled.
Figure 3:
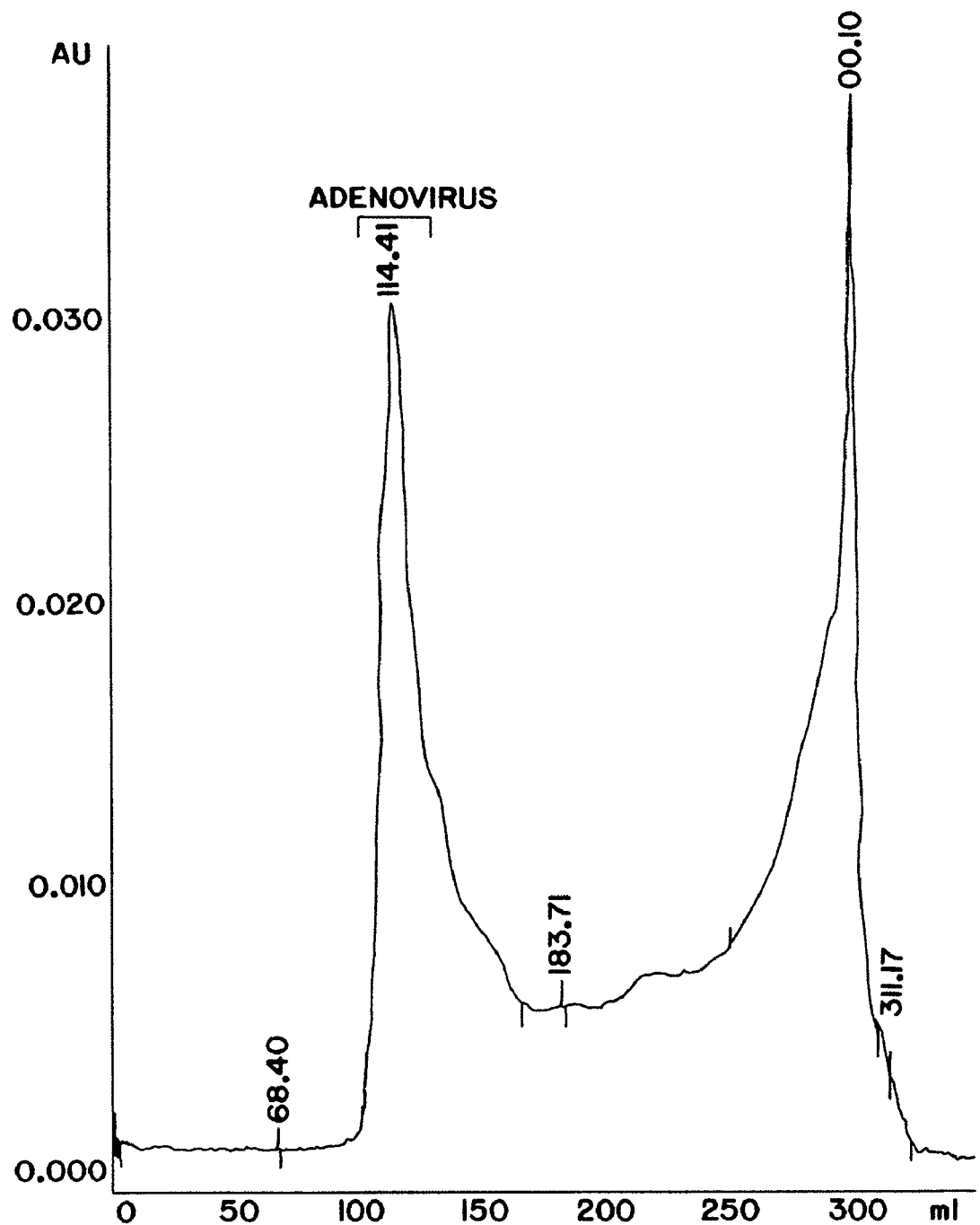
FIG. 3: Chromatogram showing elution profile of adenovirus from Superdex® 200 resin. Elution peak for adenovirus is labelled.
Figure 4:
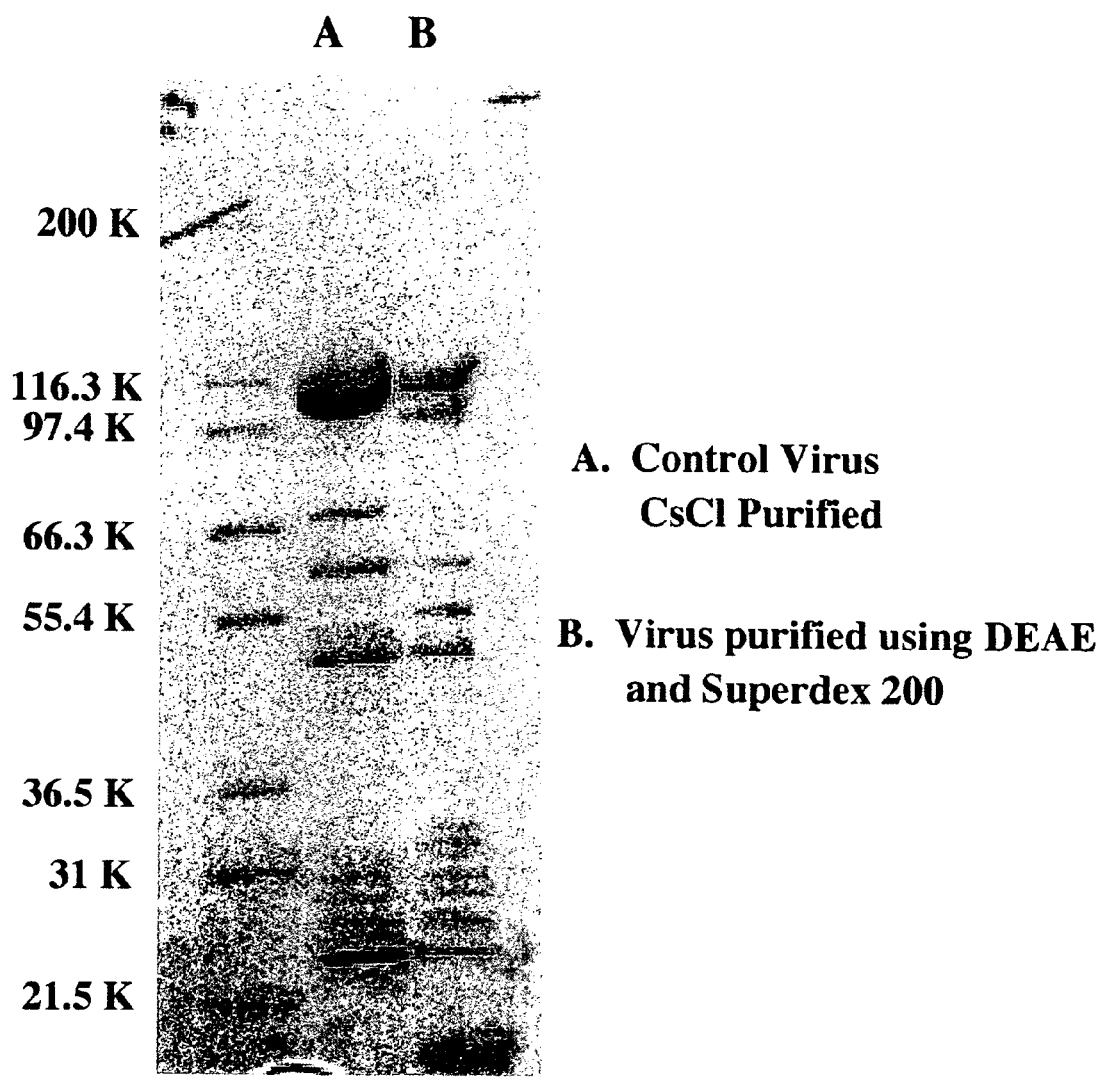
FIG. 4: SDS-PAGE analysis of adenovirus purified by DEAE and gel filtration chromatography (Lane A), compared to CsCl gradient purified virus (Lane B).

FIG. 2 shows a typical elution profile of adenovirus from DEAE MemSep® resin following chromatography of a 293 cell lysate containing adenovirus. All of the adenovirus bound to the DEAE resin and was eluted with a salt gradient applied to the resin (represented by the sloping line). Adenovirus eluted from the resin between 500-700 mM NaCl as indicated on the elution profile. This peak contained less than 10% of the total protein in the initial whole cell lysate, while typically 60-100% of the adenovirus activity was recovered. Further purification of this eluted fraction was achieved by gel filtration chromatography using a Superdex® 200 resin. Fractions from the DEAE column which had the highest virus titers were pooled, concentrated using an Amicon stir cell and applied to the Superdex® resin. Adenovirus eluted in the void volume of the resin (FIG. 3). Approximately 50-70% of the adenovirus activity was recovered in this fraction. Protein estimation (BCA) (Pierce Chemical Co.) on all of the fractions eluted from the column indicated that the gel filtration step removed approximately 70% of contaminating cellular proteins. FIG. 4 shows an SDS-PAGE analysis of adenovirus purified by a combination of DEAE and gel filtration column chromatography compared to adenovirus purified by a prior art cesium chloride method. There were some additional protein bands present in the adenovirus purified by column chromatography. To achieve further purification of the adenovirus other resins were evaluated for their ability to remove these contaminating proteins.

EXAMPLE 3

Hydrophobic Chromatography

Methods

Four different types of hydrophobic resins were tested for their ability to remove contaminants from the adenovirus preparations of Example 2: BioRad Macroprep® columns (butyl and methyl) and Tosohaus® 650 M, 65 µm (phenyl and ether). Adenovirus was applied to each hydrophobic resin in 10 mM sodium phosphate buffer, pH 7.5 containing 2 M NaCl. Bound proteins were eluted from the resin using 0.15 mM $KH_2 PO_4$, 15 mM NaCl, 0.5 mM $Na_2 HPO_4$ pH 7.5.

Results

SDS-PAGE analysis of the flow-through and eluted fractions showed that there was little separation of the adenovirus from other cellular components using these resins.

EXAMPLE 4

Cation Exchanse Resins

Methods

CM and SP MemSep® Cartridges (Millipore, Bedford, Mass.), Fractogel® $SO_3$ (a tentacle ion-exchange resin, EM Sciences), and BioRad Macroprep S® were separately equilibrated in 10 mM sodium phosphate buffer pH 7.5, containing 25 mM NaCl, 2 mM $MgCl_2$, 10% glycerol and 0.05% Tween-80. Cell lysates from 293 cells infected with adenovirus were applied to each of the resins in the same buffer containing 0.25% Tween-80. The columns were washed with 10 mM $Na_2 HPO_4$, 100 mM NaCl, 100 mM KCl, and bound proteins were eluted from the resin using a linear gradient (100 mM–1 M) of KCl and NaCl in 10 mM $Na_2HPO_4$, pH 7.5, 10% glycerol, 0.05% Tween-80 and 50 µM $ZnCl_2$. The results of the Macroprep S® chromatography are shown in Table 5.

EXAMPLE 5

Cellufine® Sulfate Resin (Amicon)

Methods

For all experiments with the Cellufine® sulfate resins (Amicon, Beverly, Mass.), cell lysate from 293 cells infected with adenovirus was applied to the resin in a solution of 25 mM NaCl and 10 mM sodium phosphate, pH 7.5, containing also 10% glycerol (w/v), 0.05% Tween-80, 2 mM $MgCl_2$, 50 µM $ZnCl_2$. Bound proteins were eluted from the resin using a linear salt gradient (100 mM–1 M) of NaCl and KCl in 10 mM $Na_2 HPO_4$ pH 7.5, 10% glycerol, 0.05% Tween-80 and 50 µM $ZnCl_2$. Both the flow through and eluted fractions were assayed for adenoviral DNA and immunoblotted using an anti-adenoviral antibody as described below.

Results

The resin which gave the most significant purification, Cellufine® sulfate, did not however lead to a purified product in which most of the adenovirus was present in an active form. Cellufine® sulfate comprises a cellulose matrix with sulfonate groups esterified at the number –6 carbon of the repeating glucose subunits (P. F. O'Neil et al., *Biotechnology*, 11, 1993, pp.173-178). Binding of proteins to this resin is thought to occur through the polysaccharide moieties thereof. Because adenovirus is a non-enveloped virus with no surface glycoproteins, it was thought that it should not bind to this resin while most cellular glycoproteins, present as contaminants, would.

Table 3 shows the results for recovery of activity of adenovirus following chromatography on the Cellufine® sulfate. Adenoviral protein and DNA were recovered in the flow through volume, as predicted, but less than about 10% of adenoviral activity was recovered in this fraction. Inactivation of the virus during chromatography on Cellufine® sulfate may have been a result of adverse interaction/partitioning involving the pores of the beads of the resin, which have a mean diameter of about 80 nm.

EXAMPLE 6

Heparin Resins

Methods

Each of the following heparin resins were assessed for their ability to purify adenovirus: Heparin Sepharose® CL6B (Pharmacia), Heparin Agarose (4% cross linkage, Sigma), HiTrap Heparin® (Pharmacia), Heparin Superflow Plus® (6% cross linkage, Sterogene), Heparin, ACTI-MOD® cartridge® (American International Chemical Inc.).

For all experiments with the heparin resins, cell lysate from 293 cells infected with adenovirus was applied to the resin in a solution of 25 mM NaCl and 10 mM sodium phosphate, pH 7.5, containing also 10% glycerol (w/v), 0.05% Tween-80, 2 mM $MgCl_2$, 50 µM $ZnCl_2$. Bound proteins were eluted from the resin using a linear salt gradient (100 mM–1 M) of NaCl and KCl in 10 mM $Na_2$ $HPO_4$ pH 7.5, 10% glycerol, 0.05% Tween-80 and 50 µM $ZnCl_2$. Both the flow through and eluted fractions were assayed for adenoviral DNA and immunoblotted using an anti-adenoviral antibody as described below.

Results

In order to further understand the causes for the disappointing performance of Cellufine® sulfate, the performance of heparinated polymers (resins) was also examined. Heparin, like Cellufine®R sulfate, is a sulfonated polysaccharide and would be predicted to have certain binding characteristics in common. Unlike Cellufine® sulfate, however, it is commercially available in one or more forms cross-linked to a variety of different beaded resins of various pore size. Table 3 shows the results of screening various heparin-linked resins. All of the resins tested bound >40% of the cellular proteins (as determined by BCA) that contaminated the virus samples, but the only resin which gave 100% recovery of active virus was the Sterogenee heparin agarose, a 6% cross-linked agarose. Generally speaking, a 6% agarose matrix with an exclusion limit of about 6 million daltons would have smaller pores than, for example, an agarose gel with 4% cross-linkage and an exclusion limit of about 20 million daltons. It is possible that, because of its average pore size, the 6% cross-linked agarose excluded the adenovirus completely during chromatography. As a result, active adenovirs was recovered in the flow-through fraction.

TABLE 3

Recovery of Active Adenovirus following Chromatography with Cellufine ® Sulfate and Heparin Resins

| Resin | I.U. before Chromatography | I.U. after Chromatography | % Activity Recovered |
|---|---|---|---|
| Heparin Sepharose ® CL6B | $2.1 \times 10^{10}$ | $5.7 \times 10^9$ | 27 |
| HiTrap ® Heparin | $5.8 \times 10^{10}$ | $3.8 \times 10^9$ | 7 |
| Heparin Agarose, 4% X-link | $5.8 \times 10^{10}$ | $9.2 \times 10^9$ | 16 |
| Heparin Superflow ® Plus 6% x-link agarose | $5.1 \times 10^9$ | $1.3 \times 10^{10}$ | 100 |
| Cellufine ® Sulfate | — | — | 10 |

Figure 5:
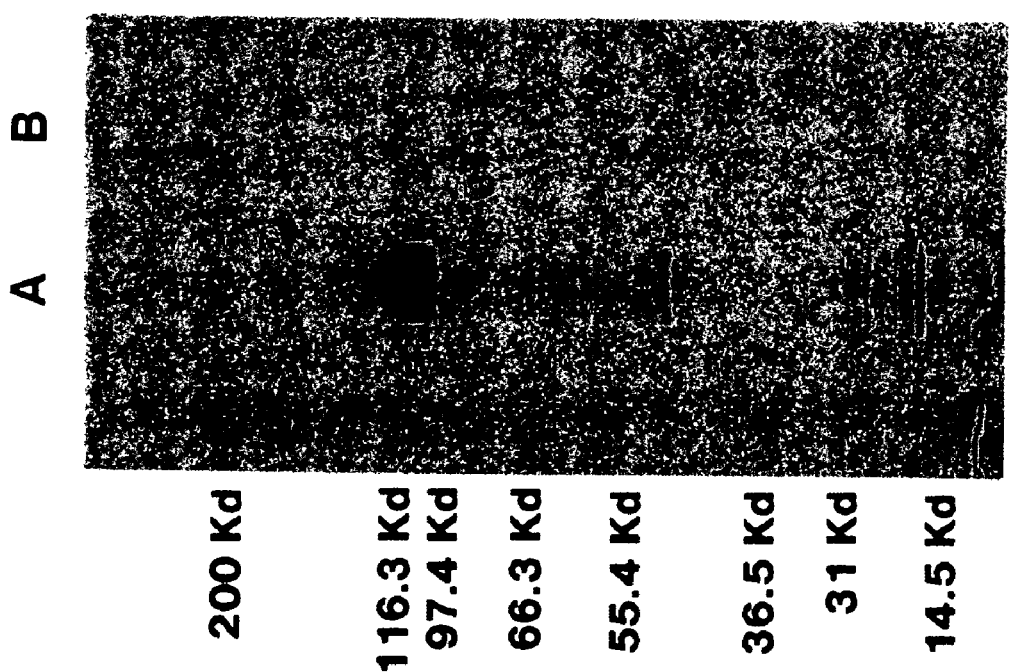
FIG. 5: SDS-PAGE analysis of adenovirus purified by heparin, DEAE and Superdex® chromatography (Lane B), compared to CsCl gradient purified virus (Lane A).
Figure 6A:
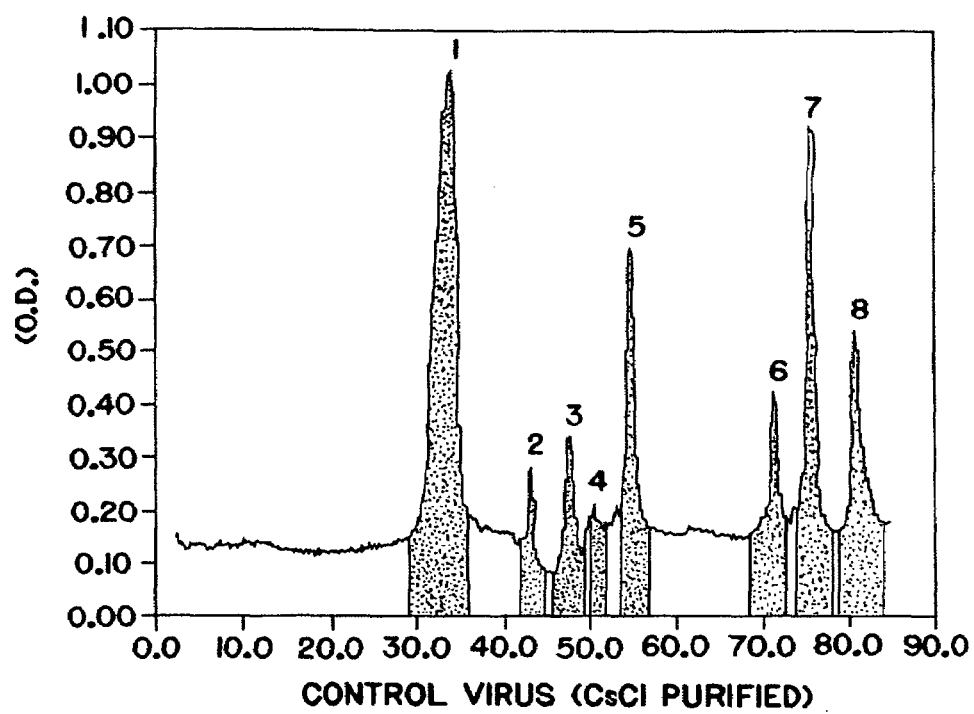
FIG. 6: Densitometric analysis of adenovirus purified by heparin, DEAE and Superdex® chromatography B, compared to CsCl gradient purified virus A.
Figure 6B:
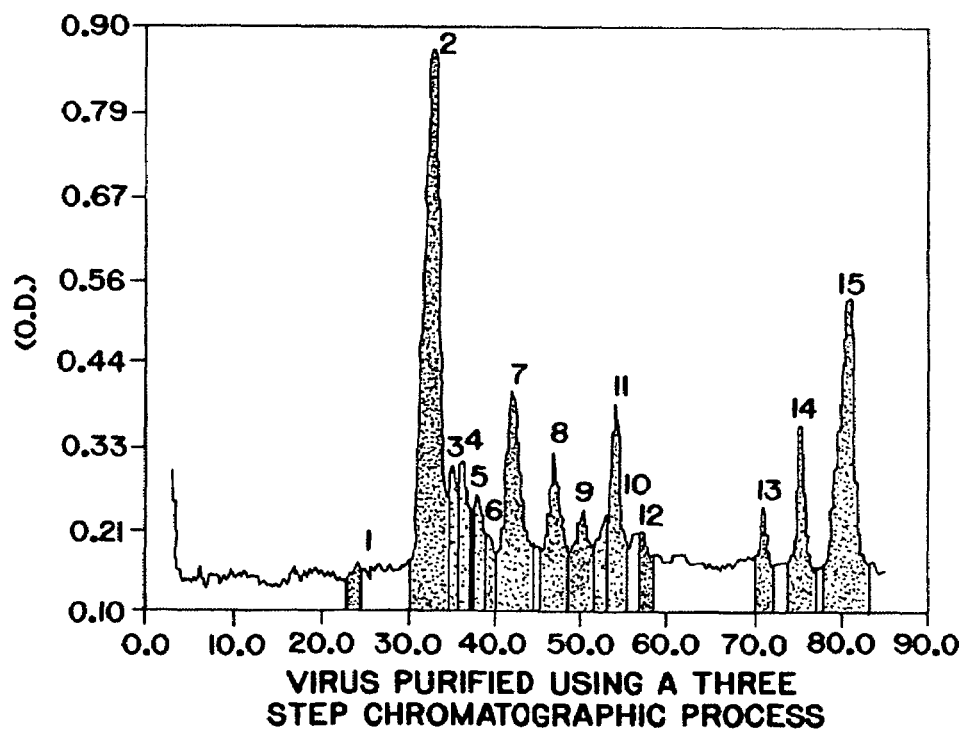

Lysate from 293 cells infected with adenovirus was chromatographed using a heparin ACTI-MOD® disc as described above. Adenovirus was recovered in the flow through fraction and purified further using a combination of DEAE ion exchange and gel filtration chromatography. SDS-PAGE analysis of the adenovirus fraction from the GF column showed that the purity of the adenovirus (purified by column chromatography) was as pure as the control adenovirus purified by CsCl centrifugation (FIG. 5). FIG. 6 shows a densitometric analysis of the fractions analyzed in FIG. 5.

EXAMPLE 7

Biorad Ceramic Hydroxyapatite (80 µm Pore Size)

The BioRad hydroxyapatite column was equilibrated with 10 mM sodium phosphate pH 7.5 containing 25 mM NaCl, 1 mM $MgCl_2$, and 10% glycerol. Adenovirus or AAV was applied to the resin in the same buffer. Bound proteins were eluted from the resin using an increasing linear salt gradient from 10 to 300 mM of sodium phosphate, all at pH 7.5.

EXAMPLE 8

Partitioning Polymers

A series of partitioning polymers (resins) were screened for their ability to purify active adenovirus (Table 4). It was found that the majority of the polymers tested gave significant purification, but use of only a few led to recovery of purified adenovirus in an active form. In general, the membrane-based cartridge polymers (resins), such as the MemSep® cartridge from Millipore or the ACTI-MOD® cartridge (American Chemical International) gave a better recovery of active virus. The superior performance of these products is believed attributable to the open macroporous structure of the membrane matrix in these cartridges [in these preferred examples, DEAE groups are covalently linked to the polymer matrix cellulose in the case of MemSep®, or to silicate in the case of ACTI-MOD®]. This type of macroporous structure [having openings (pores) of about 12,000 A°, or 1.2 µm, in width] allows rapid passage of the adenovirus virions which have diameters of about 140 nm (including fibre).

Table 5 is a summary chart of various chromatographic methods for adenovirus purification.

TABLE 4

Recovery of Active Adenovirus from Different Types of Resins

| Type of Resin | Pore Size | Activity Recovered |
|---|---|---|
| Membrane Based (MemSep ® or ACTI-MOD ®) | 1 µm | 100% |
| Macroporous (BioRad) | 0.08-0.1 µm | 10% |
| Tentacle (EM Science) | ND | <10% |
| 4% Agarose | ND | <20% |
| 6% Agarose | ND | 100% |

TABLE 5

Results of Resin Screen

| RESIN | TYPE | CLEAN-UP | ACTIVITY |
|---|---|---|---|
| Sperilose Sulfate (ISCO) | Cross-linked cellulose | good | 62% |
| Heparin Superflow Plus | 6% cross-linked | good | 80% |
| POROS PI | 6000-8000 A thru-pores | fair | 5% |

TABLE 5-continued

Results of Resin Screen

| RESIN | TYPE | CLEAN-UP | ACTIVITY |
|---|---|---|---|
| Fractogel DEAE (EM Sciences) | "tentacles" rather than pores | good | 35% |
| DEAE MemSep ® | Membrane based | good | 80% |
| SartoBind DEAE (Sartorius) | Membrane based | good | 30% |
| PolyFlo ® (Puresyn) | non-porous | excellent | 4%* |
| Heparin Agarose (Sigma) | 4% cross-linked agarose | good | 16% |
| HiTrap Heparin (Pharmacia) | cross-linked agarose | good | 7% |
| Heparin CL6B | cross-linked agarose | good | 16% |
| Cellufine ® Sulfate (Amicon) | MacroPorous | good | <10% |
| Hydroxyapatite (BioRad) | calcium phosphate | good | <10% |
| MacroPrep S (BioRad) | Macroporous | | 40%** |

*Purification of adenovirus on the PolyFlo resin involves low salt and organic elution.
**Batch Process

EXAMPLE 9

Purification of Adeno-Associated Virus (AAV)

One of the main problems associated with using AAV as a vector in gene therapy is production of sufficient quantities of the virus. Currently AAV is purified by density gradient ultracentrifugation techniques, which generally results in very low yields (0.3-5%) of active virus. However density gradient ultracentrifugation is very effective in separating AAV from adenovirus, which is used as a helper virus in propagating AAV in 293 cells. The present invention provides combining an improved method for extraction of AAV from infected cells with column chromatography steps to increase the yield of AAV.

Figure 7A:
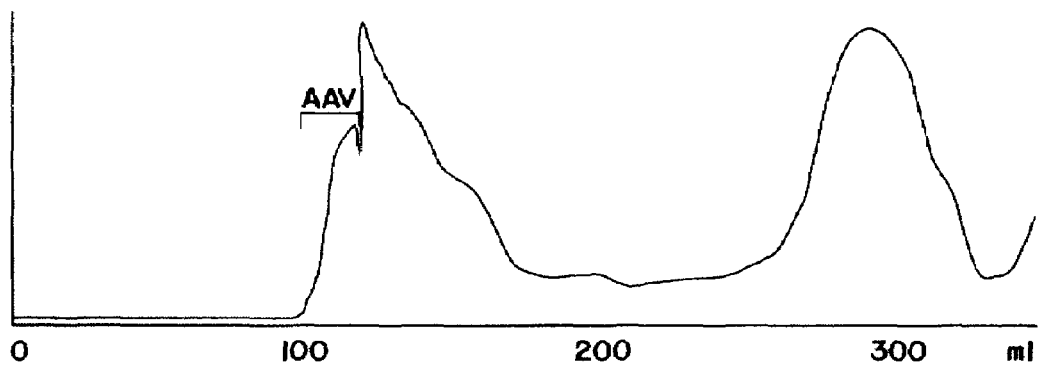
FIG. 7: Chromatogram showing elution profiles of AAV from (A) Superdex® 200 resin and (B) DEAE-MemSep® resin.

Improved extraction of AAV from infected 293 cells was achieved by pressure lysis of the cell in the presence of detergent (Tween-80). Following clarification of the lysate as provided above in Example 1, AAV was separated from other cellular proteins by gel filtration chromatography. FIG. 7a shows the elution profile from a Superdex® 200 resin Pharmacia) following chromatography of AAV infected 293 cell lysate. The void volume peak contains the majority of the AAV as detected by slot blot analysis and immunoblotting of this fraction.

Figure 7B:
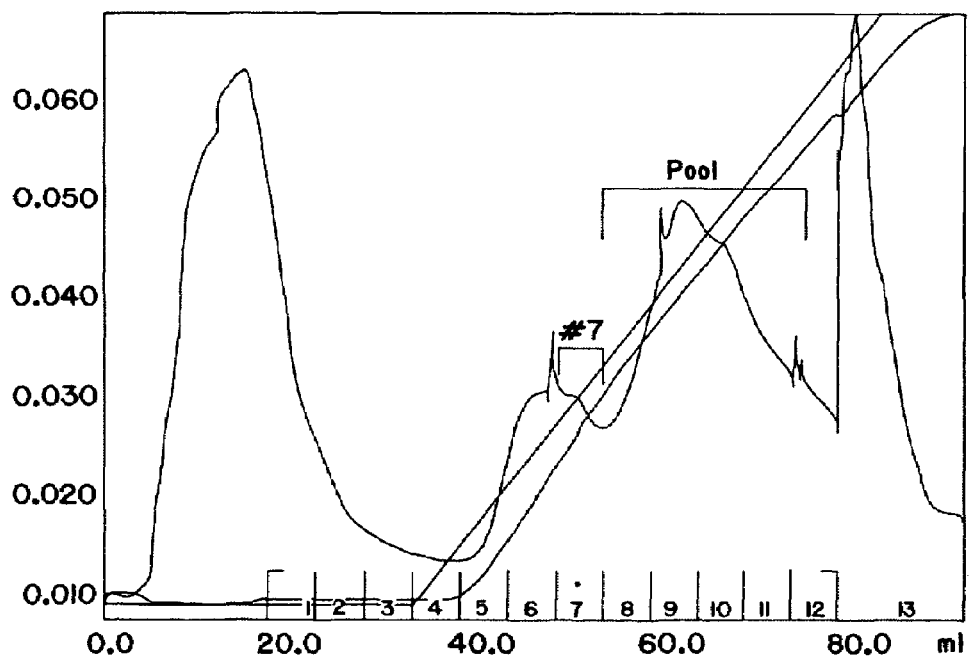
Figure 8:
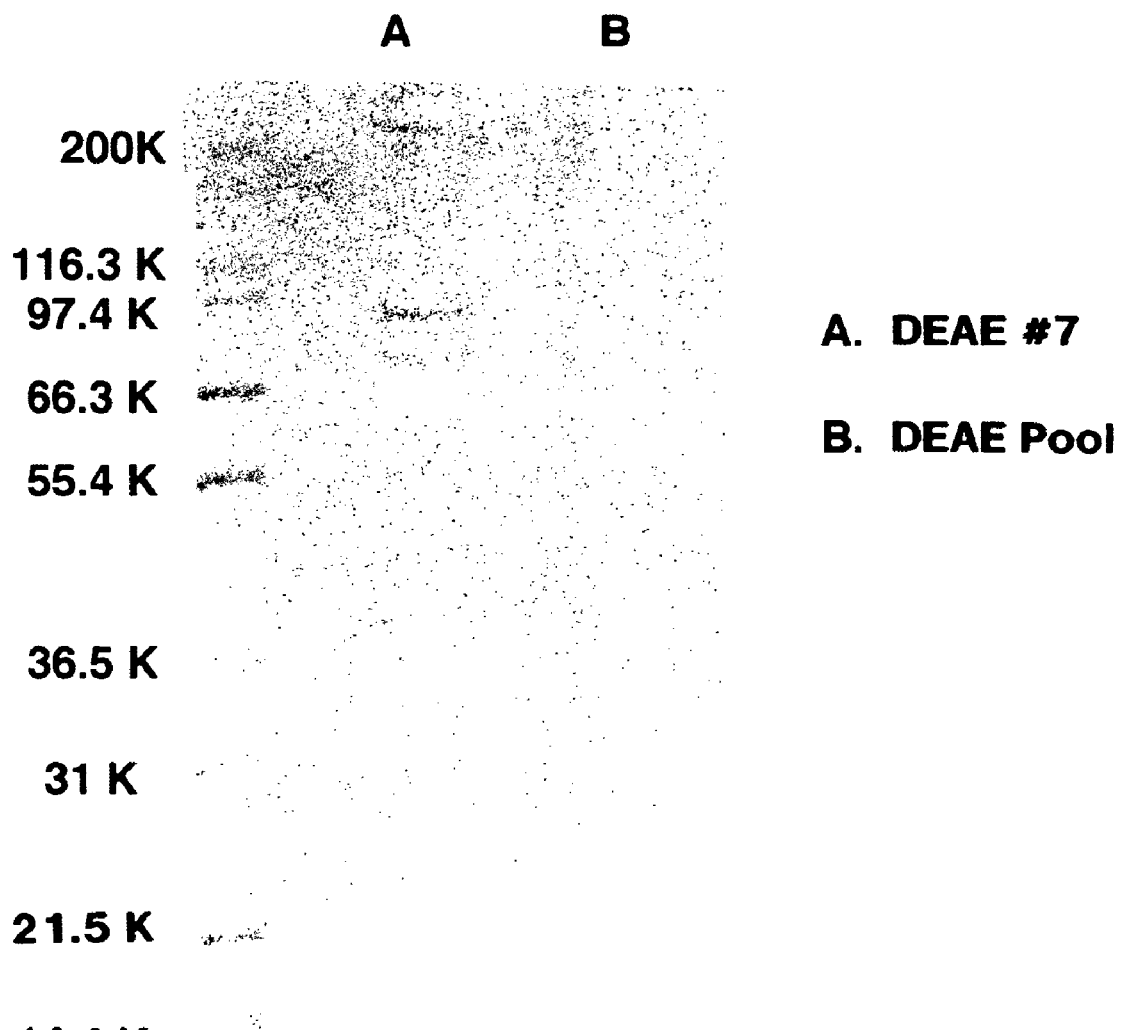
FIG. 8: SDS-PAGE analysis of two fractions of AAV purified by Superdex® and DEAE chromatography (Lanes A and B).

Further purification of this peak was achieved by ion-exchange chromatography using a DEAE-MemSep® cartridge. The DEAE column was very effective in separating AAV from adenovirus. Under the conditions used (10 mM sodium phosphate pH 7.5 containing 25 mM NaCl, 10% glycerol and 0.05% Tween-80), both AAV and adenovirus bound to the DEAE-resin. When a linear salt (KCl and NaCl) gradient was applied to the resin, AAV eluted at 200 mM salt (FIG. 7, panel B), while the adenovirus remained more tightly bound to the resin and was eluted later in the gradient at 500-700 mM NaCl (FIG. 7, panel B). Therefore, AAV and adenovirus can be effectively separated from one another using DEAE ion-exchange chromatography. SDS-PAGE analysis of two DEAE fractions containing AAV is shown in FIG. 8. The activity of AAV in the DEAE fraction #7 was $6.5 \times 10^7$ i.u./ml or a total of $3.8 \times 10^8$ i.u. The activity of AAV in the DEAE pool fraction was $1.38 \times 10^7$ i.u./ml or a total of $2.76 \times 10^8$ i.u. Collectively, these fractions provide recovery of approximately 100%, of the AAV infectious units applied to the DEAE resin.

EXAMPLE 10

Extraction of AAV from 293 Cells

The human embryonal cell line (293) was also used to propagate the AAV. Virally infected cells were incubated until the cell monolayer exhibited extensive cytopathic effects (CPE). The cells were harvested and collected by centrifugation at 1000×g. Cell pellets were frozen at 80° C. for further use or were resuspended in 10 mM NaPi, 10 mM NaCl, 10% glycerol, 2 mM $MgCl_2$, pH 6.4.

Following resuspension, the cells were treated with benzonase® for 1 hour at room temperature followed by trypsin treatment in the presence of 1% Tween-80. The cells were then lysed using a Microfluidiser (Microfluidics, Newton, Mass.) at 1000 psi. The resulting lysate was clarified to remove cellular debris by vacuum filtration through a 3.0 μm glass fiber filter (Microfiltration Systems), followed by a further filtration step using a 0.8 μm cellulose acetate filter (Microfiltration Systems) or filtered through a 0.45 μm 15 Millex® HV (Millipore) filter unit before chromatography.

EXAMPLE 11

Chromatographic Purification of AAV

Various chromatography resins were tested for effective AAV purification characteristics using a Pharmacia FPLC. The following series of chromatography steps were found particularly useful.

a) BioRad Ceramic Hydroxyapatite (80 μm Pore Size)

Cell lysates from 293 cells infected with AAV (in the presence of adenovirus) (Example 10) were chromatographed on a BioRad a hydroxyapatite column, which was pre-equilibrated with 10 mM $Na_2 HPO_4$, pH 6.4, containing 10 mM NaCl and 10% glycerol. AAV was applied to the resin in the same buffer. Bound proteins were eluted from the resin using an increasing gradient from 10 to 400 mM sodium phosphate, at pH 6.4. Fractions collected from the resin were assayed for AAV DNA using a slot blot assay and AAV proteins by immunoblotting using an antibody (Catalog 03-65158, from American Research Products, Belmont, Mass.) against the three capsid proteins of AAV-VPI, VP2 and VP3. Fractions eluted from the resin were also analyzed for adenoviral contaminating proteins by immunoblotting using an anti-adenoviral antibody.

Figure 9:
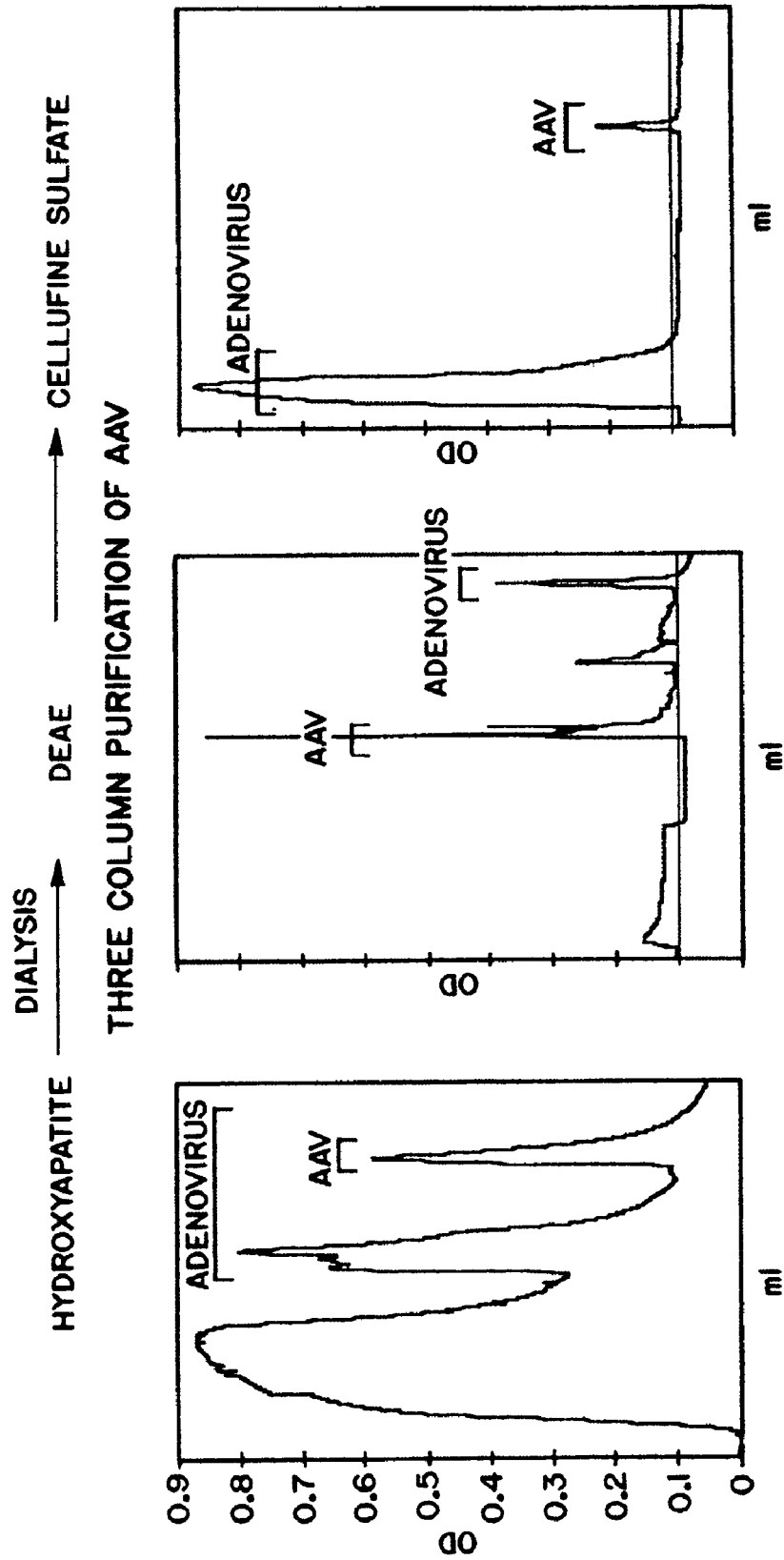
FIG. 9A: Ceramic hydroxyapatite chromatography of an AAV/adenovirus-containing 293 cell lysate. Elution peaks for both AAV and adenovirus are labelled.
FIG. 9B: DEAE-MemSep® chromatography of an hydroxyapatite AAV-containing eluate. Elution peaks for both AAV and adenovirus are labelled.
FIG. 9C: Cellufine® sulfate Chromatography of an AAV-containing DEAE eluate. The eluted AAV peak from the resin is labelled.

FIG. 9A shows a typical elution profile of a ceramic hydroxyapatite (CHA) resin following chromatography of a 293 cell lysate containing AAV and adenovirus. All of the AAV and adenovirus bound to the CHA resin and was eluted when a phosphate gradient was applied to the resin. AAV eluted from the resin at 125 mM phosphate as indicated on the elution profile. This peak contained less than 20% of the total protein in the initial whole cell lysate while typically 80% of the AAV activity was recovered. The eluted AAV peak also contained some contaminating adenoviral proteins as measured by immunoblotting and by titre analysis (Table 5).

b) DEAE Chromatography (Anion Exchange)

In order to separate AAV from the adenovirus, ion exchange chromatography using a DEAE-MemSep® column was used. A DEAE MemSep® 1010 HP (Millipore) column (5 ml) was equilibrated with 10 mM phosphate buffer containing 50 mM NaCl, 10% glycerol, pH 7.5. AAV-containing fractions eluted from the hydroxyapatite column (above) were pooled and dialyzed into the same buffer used for equilibration of the DEAE resin. A linear salt gradient (50 mM–2 M) of KCl and NaCl in 10 mM $Na_2HPO_4$ pH 7.5, and 10% glycerol was applied to the resin at a flow rate of 5 ml/min. Bound proteins were eluted from the resin and collected in 2.5 ml fractions. AAV eluted at 200 mM salt while adenovirus eluted at 500-700 mM salt. Each fraction was monitored for a) AAV proteins (Coomassie blue staining and immunoblotting); b) AAV DNA; c) contaminating adenoviral proteins; and (d) infectivity.

Under the conditions used (10 mM sodium phosphate, pH 7.5, containing 50 mM NaCl, 10% glycerol and 0.05% Tween-80) both AAV and adenovirus bound to the DEAE-resin. When a linear salt gradient was applied to the resin, AAV eluted at 200 mM salt (FIG. 9B) while the adenovirus remained more tightly bound to the resin and was eluted later in the salt gradient at 500-700 mM NaCl (FIG. 9B). Therefore AAV and adenovirus can be effectively separated using anion exchange (DEAE) chromatography. The recovery of activity of AAV from the DEAE-MemSep® was 75% (Table5). SDS-PAGE analysis of the pooled-MV containing fraction from the DEAE resin (FIG. 10, lane 3) showed that there were still some contaminating proteins present so this fraction was purified further using a Cellufine® sulfate resin. Lanes 1-4 represent equal percentages of each fraction (0.5%) and show the recovery of MV proteins throughout the purification. Lane 5 represents a larger percentage of the final MV containing fraction and gives a more intense staining of the MV proteins VP1, VP2 and VP3. Fractions which were positive for both AAV DNA and protein were pooled and chromatographed further using a Cellufine® sulfate resin (below).

c) Cellufine® Sulfate Resin (Amicon)

Cellufine® sulfate resin was equilibrated with PBS containing 10% glycerol. Fractions eluted from the DEAE resin which contained AAV proteins and DNA were pooled and applied to the resin at a flow rate of 1 ml/min. The resin was washed with 250 mM NaCl and a linear salt gradient of 0.25-1 M NaCl in PBS/glycerol was applied. The material eluted from the resin using this salt gradient and the flow through fraction were both analyzed for a) AAV proteins (immunoblotting); (b) AAV infectivity (titre analysis); and c) adenovirus proteins (immunoblotting) and adenovirus infectivity (titre analysis). Under the buffer conditions used, AAV bound to the resin and was eluted at 475 mM salt (FIG. 9C). Adenoviral protein and DNA were recovered in the flow through fraction.

Figure 10:
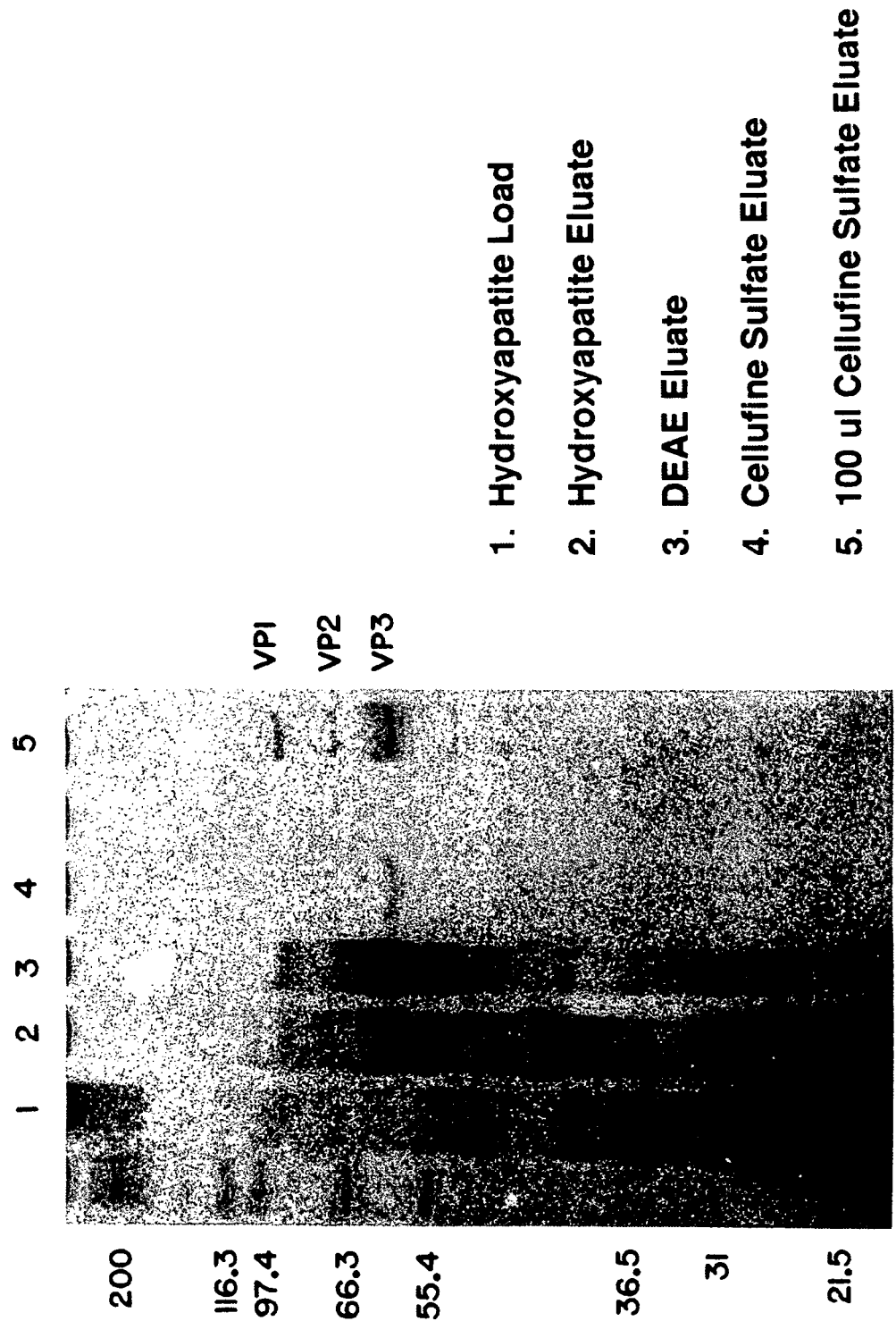
FIG. 10: Coomassie-stained SDS-PAGE analysis of the AAV containing fractions recovered from various columns: lane 1: hydroxyapatite load; lane 2: hydroxyapatite eluate; lane 3: DEAE eluate; lane 4: Cellufine® sulfate eluate; and lane 5: Cellufine® sulfate eluate (100 µl). Control protein standards (in kD) are shown in the left column.
Figure 11:
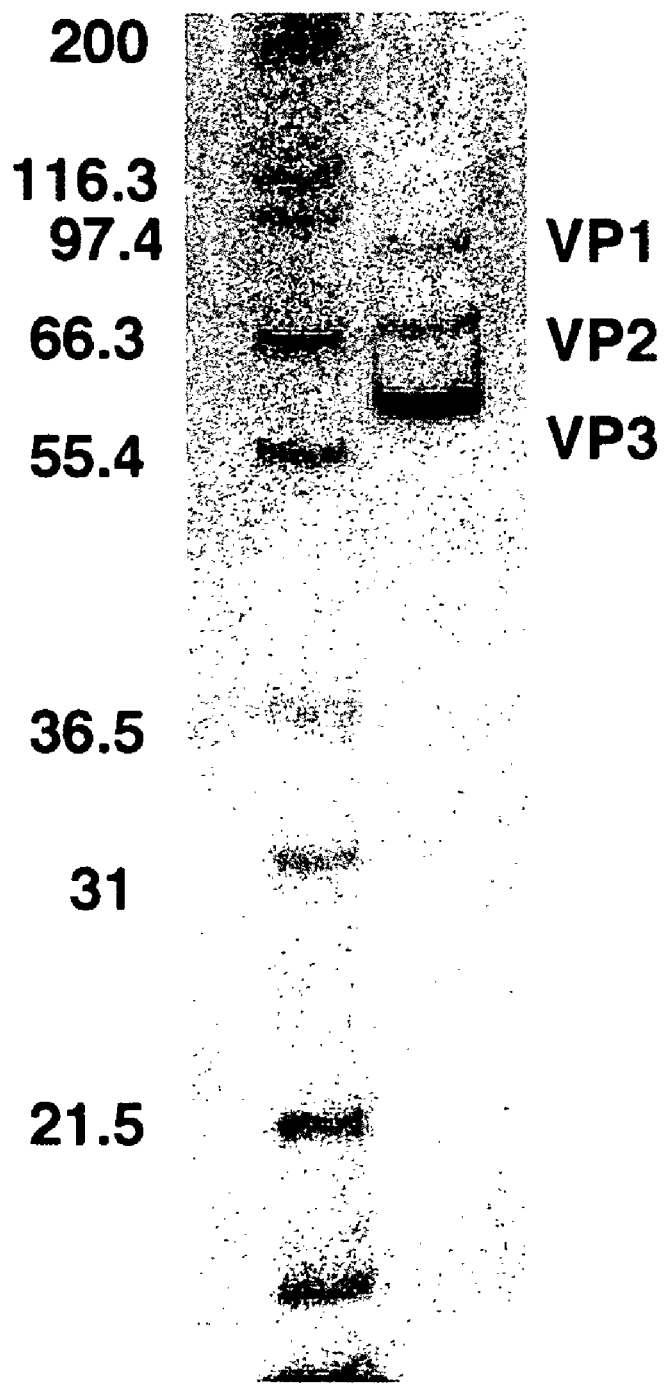
FIG. 11: SDS-PAGE analysis of AAV purified by ceramic hydroxyapatite, DEAE and Cellufine® sulfate chromatography.
Figure 12:
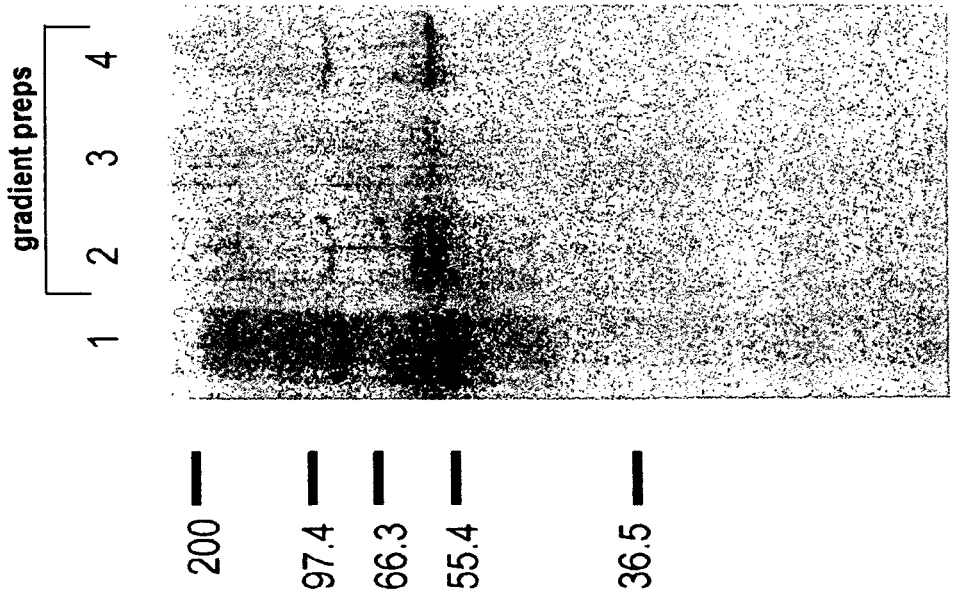
FIG. 12: Coumassie-stained protein gel of AAV purified by ceramic hydroxyapatite, DEAE and Cellufine® sulfate chromatography (Lane 1), compared to CsCl gradient purified AAV (Lanes 2-4).
Figure 13:
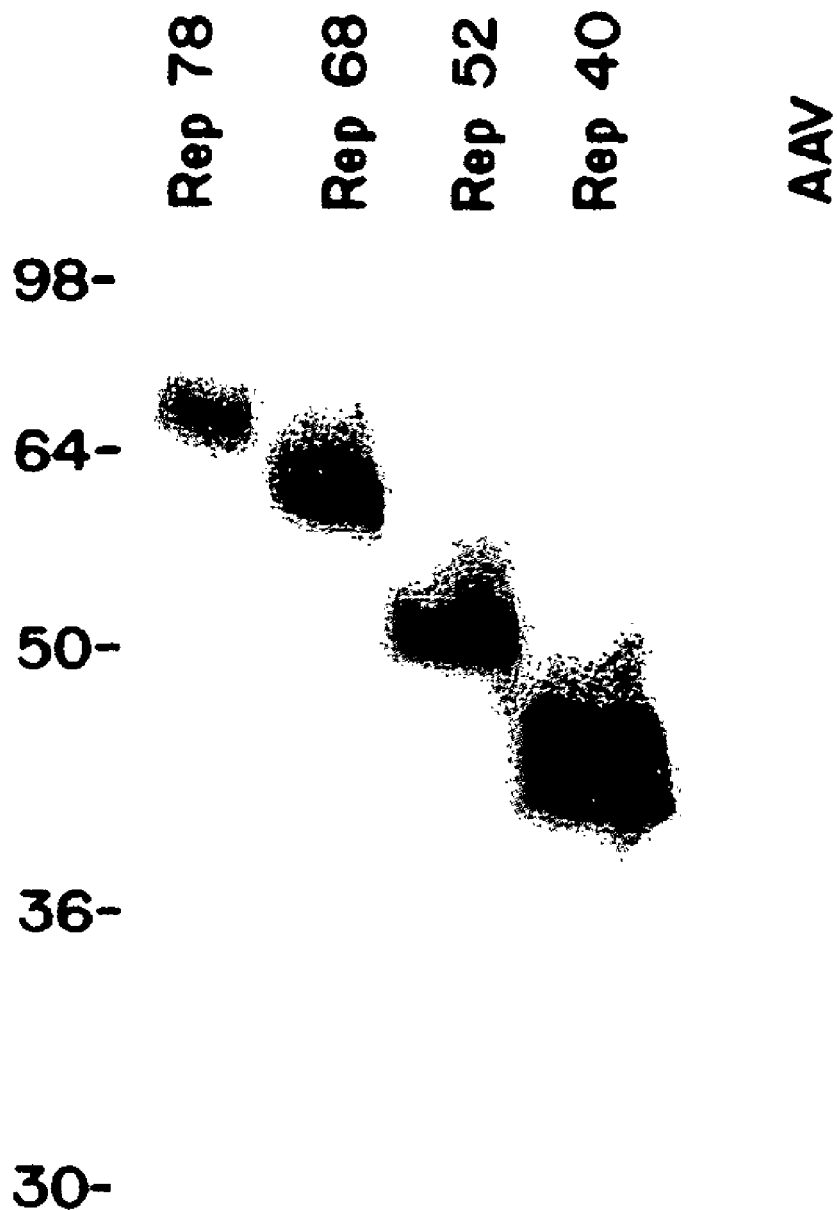
FIG. 13: Immunoblot of AAV purified by ceramic hydroxyapatite, DEAE and Cellufine® sulfate chromatography (Lane AAV), using an anti-Rep antibody, compared to Rep controls.

Table 5 shows the recovery of AAV activity from several purification runs. FIG. 10 shows Coomassie Blue-stained SDS-PAGE results of the purification from each column. The three column purification procedure described above provided an AAV yield of 48% and a purity of >90% pure (FIG. 11). FIG. 12 is a Coomassie stained gel comparing AAV purified using the CsCl gradient method and AAV purified using the CsCl gradient method and AAV purified using the column purification procedure of the present invention. This gel shows that the AAV purified using both methods is of comparable purity. In addition, the AAV purified by the above procedure was shown to be free of Rep proteins (FIG. 13). FIG. 13 shows an immunoblot (using an anti-Rep antibody) of the column-purified AAV along with known Rep standards. Approximately 71% of the AAV activity is recovered in the Cellufine sulfate eluate while less than 15 1% of the adenovirus activity is recovered in the same fraction.

Cellufine® sulfate thus has two main uses: a) it reduces the level of contaminating adenovirus in AAV preparations and b) it concentrates the AAV containing fraction. However, despite the fact that the level of contaminating adenovirus is reduced following Cellufine® sulfate chromatography there still remains some low level adenovirus activity ($6.73 \times 10^3$ IU/ml).

d) Zinc Chelate Chromatography

In order to completely remove all of the contaminating adenovirus a further chromatography step using zinc chelate chromatography was employed. The interaction of virions with metals has been inferred from studies of viruses and bacteriophages. Previous studies from the inventors' laboratory showed that adenovirus can adsorb to a zinc metal affinity column.

The final fraction of purified AAV recovered from the Cellufine® sulfate resin was analyzed by SDS-PAGE, followed by immunoblotting using an anti-adenovirus antibody. This was to determine the level of contamination of adenovirus in the final AAV-containing fraction. Immunoblotting showed that there was no detectable adenoviral proteins, while titre analysis showed that there was some. adenoviral activity in this fraction even though it only accounted for 1% of the total activity (Table 6).

The immobilized zinc column was prepared for metal charging by washing the column sequentially with one volume of 100 mM EDTA and one volume of 0.2 M NaOH. The matrix was charged with zinc by washing with 100 mM $ZnCl_2$ in water acidified with glacial acetic acid. The column was then washed with water and equilibrated with 50 mM Hepes pH 7.5, containing 450 mM NaCl, 2 mM $MgCl_2$ and 0.05% Tween-80. The AAV-containing fraction eluted from the Cellufine® sulfate resin was applied to the zinc chelate resin. After loading, the column was washed with a ten column volume linear gradient from 50 mM Hepes, pH 7.5, containing 450 mM NaCl, 2 mM $MgCl_2$, 10% glycerol and 0.05% Tween-80 to 50×nM Hepes containing 150 mM NaCl, 2 mM MgCl, 10% glycerol and 0.05% Tween-80. Elution was performed with a linear (0-500 mM) glycine gradient in 150 mM NaCl, 50 mM Hepes, pH 7.5, 2 mM $MgCl_2$, over ten column volumes.

The AAV containing fraction eluted from the Cellufine® sulfate resin was applied to the zinc chelate resin in 450 mM NaCl. The flow through fraction was collected and bound proteins were eluted using a glycine gradient. SDS-PAGE analysis of the flow through fraction showed that all of the AAV was recovered in the flow through while immunoblots using an anti-adenovirus antibody showed that the adenovirus had bound to the zinc chelate resin and was eluted in the presence of an increasing gradient of glycine. Initial experiments using zinc chelate chromatography indicates that it can be a useful resin for the separation of AAV and adenovirus. The purification procedure yielded AAV which was greater than 70% pure with an overall yield of 30%-40%.

TABLE 6

Summary of AAV Chromatographic Purification Column Performance: Total Protein

| Sample | Total Protein | % Protein Remaining[1] | % Protein (cumulative)[2] |
|---|---|---|---|
| HA Load | 180 mg | 110 | 100 |
| HA Eluate | 20 mg | 11 | 11 |
| DEAE Eluate | 6 mg | 30 | 3 |
| CS Eluate | 0.5 mg | 8 | 0.4 |

[1]Individual column performance
[2]Overall performance

Column Performance: Recovery of AAV Activity

| Sample | #1 | #2 | #3 | #4 | #5* | Average |
|---|---|---|---|---|---|---|
| HA Load | | | | | | |
| HA Eluate | 84% | 86% | 60% | 100% | 100% | 88% |
| EAE Eluate | 75% | 100% | 100% | 56% | 18% | 70% |
| CS Eluate | 71% | 24% | 30% | 22% | 8% | 48% |
| Zinc FT | | 9% | 9% | | | 20% |

*not included in the average

Column Performance: Adenovirus Activity Removed

| Sample | #1 | #2 | average |
|---|---|---|---|
| HA Load | | | |
| HA Eluate | 90% | 0* | 90% |
| DEAE Eluate | 95% | 70% | 80% |
| CS Eluate | >99% | >99% | 50% |

Total 99.99% of contaminating adenovirus activity removed
*not included in the average Average Activity Recovered During Purification Runs (n=2):

| | HA Load | HA Eluate | DEAE Eluate | CS Eluate |
|---|---|---|---|---|
| Total mgs | 236 | 13 | 5 | 0.6 |
| AAV IU/ml | 3.58E+07 | 1.31E+08 | 5.4E+08 | 2.42E+08 |
| Total AAV Ius | 3.92E+09 | 7.24E+09 | 2.47E+09 | 1.11E+09 |
| AV Ius/ug | 1.66E+04 | 5.57E+05 | 4.94E+05 | 1.85E+06 |

The average adenovirus activity remaining (calculated from 2 runs) after 3 columns=4.8E+04 (+/−4E+04). Adenovirus activity represents 0.03%+/−0.015% of the total AAV activity.

EXAMPLE 12

Density Gradient Purification of Virus

Standard recombinant adenovirus or AAV virus was prepared by a three step centrifugation procedure. Infected cells were lysed by three cycles of freeze-thaw in the presence of benzonase®. Lysate was centrifuged in a table top centrifuge for 15 min at 3500 rpm at 4° C. The pellet was discarded and the supernatant was layered onto a 1.27 g/cm$^3$ CsCl and 1.4 g/cm$^3$ CsCl discontinuous step gradient and centrifuged at 26,000 rpm for 1.5 hours. The virus band was collected and mixed with 1.34 g/ml CsCl and centrifuged for at least two hours at 60,000 rpm. The viral band from this first equilibrium gradient was collected mixed with 1.34 g/ml CsCl and recentrifuged at 30,000 rpm overnight. The final virus pool from this step was dialyzed extensively against phosphate buffered saline (PBS) supplemented with 1% sucrose. Alternatively the CsCl was removed by gel filtration on a Superdex® resin (Pharmacia) as described above.

EXAMPLE 13

Detection of Adenoviral DNA Using Agarose Gels

Column fractions were first treated with 0.1% SDS for 15 minutes then digested with Pronase (Sigma) for 1 hour at room temperature. After digestion was complete, the samples were extracted twice with one volume of phenol:CHCL$_3$:isoamyl alcohol, then precipitated with two volumes of ice-cold 95% ethanol for 20 minutes at −20° C. The precipitate was pelleted at 13,000×g for 20 min at 4° C. Samples were resuspended in TE buffer (Tris, EDTA). Restriction enzyme digestion of the adenoviral DNA was performed and the digest was analyzed for diagnostic adenoviral fragments on a 0.8% agarose gel at 120 V for 4 hours or overnight at 35 V.

EXAMPLE 14

Slot Blot Analysis of Column Fractions for Detection of AAV DNA

Figure 14:
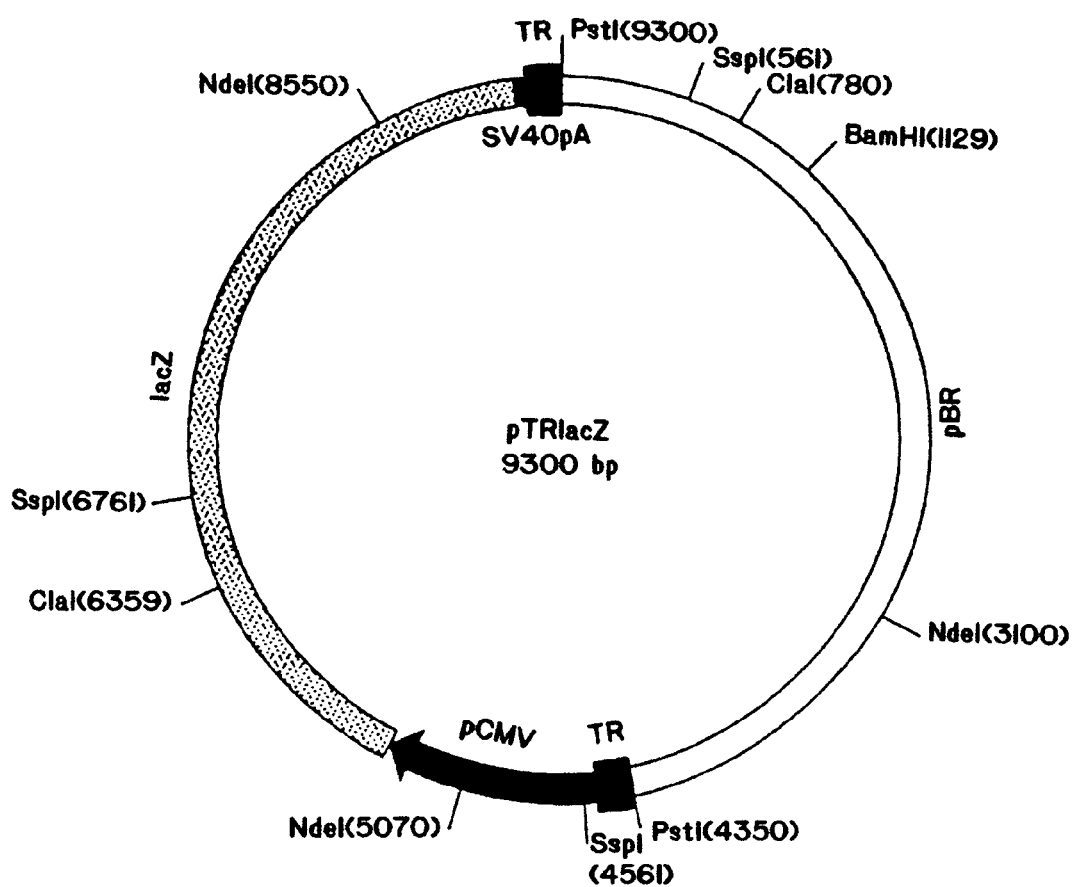
FIG. 14: Schematic diagram of pTRlacZ.

Column fractions were assayed for AAV DNA by slot blot analysis (AAV DNA was present in a vector construct provided by Dr. N. Muzyczka, University of Florida, Miami, also containing lacZ as reporter gene, see FIG. 14). Samples were incubated at 56° C. for 20 minutes to inactivate the adenovirus followed by treatment with DNaseI at 37° C. for 15 min to degrade nonvirion DNA. DNaseI was then inactivated by heat treatment at 68° C. for 10 minutes. Following Proteinase K treatment of the samples, the DNA was extracted using phenol/chloroform and precipitated with 3 M NaOAc. DNA was applied to a Gene Screen Plus membrane and, following a prehybridization and hybridization step, the membrane was probed with a P$^{32}$ random label CMV β-gal Pvu II fragment. The number of particles of AAV in the sample was calculated using a pTRlacZ DNA standard curve.

EXAMPLE 15

Virus Protein Detection

One dimensional SDS-PAGE was performed using either a 4-20% or 10-20% gradient (Daiichi) gels. Proteins in the gel were detected using Coomassie blue. For immunoblotting, PVDF membranes (Novex) were prewetted with methanol and soaked in 10 mM CAPS, pH 11, containing 10% methanol. Gels were equilibrated in this transfer buffer for 10 minutes and then blotted at 30 V for 1 hour in a Novex Blot Module. After transfer membranes were blocked with 1% dried milk in TBS (20 mM Tris-HCl, pH 7.5, containing 150 mM NaCl) for one hour. After blocking, the membranes were probed with anti-adenovirus antibody (Lee Biomolecular) or anti-VP1, VP2, VP3 (AAV) antibody in 20 mM Tris-HCl, 150 mM NaCl, pH 7.5, and 0.05% Tween 20 (TBST) containing 0.1% BSA for 2 hours. The membranes were incubated with horseradish peroxidase labeled anti-mouse IgG for 20 minutes and the immunoreactive bands visualized by chemiluminescence using the BM Chemiluminescent Western Blotting Detection System (Boehringer Mannheim).

The invention claimed is:
1. A method comprising:
   a) lysing adenovirus-infected cells to generate a whole-cell lysate comprising active adenovirus;
   b) applying said lysate to a first chromatographic matrix;

c) applying the eluate from the chromatographic matrix to a second chromatographic matrix; and
d) recovering a composition of adenovirus particles with at least 50% of the adenoviral activity of the whole cell lysate.

2. The method of claim 1, wherein the chromatographic matrix has pore sizes of less than 80 nm or greater than 140 nm.

3. The method of claim 1, wherein the pore size of the chromatographic matrix chromatographic matrix is about 1.2 μm or greater.

4. The method of claim 1, further comprising incubating the whole-cell lysate with a nuclease prior to step (b).

5. The method of claim 4, further comprising clarifying the lysate prior to step (b).

6. The method of claim 4 or 5, further comprising ultrafiltering the lysate prior to step (b).

7. The method of claim 4, wherein the nuclease is Benzonase ®.

8. The method of claim 1, further comprising clarifying the whole-cell lysate prior to step (b).

9. The method of claim 1, further comprising ultrafiltering the whole-cell lysate prior to step (b).

10. The method of claim 1, wherein step (a) comprises detergent lysis.

11. The method of claim 10, wherein the detergent is Tween-80.

12. The method of claim 1, wherein step (a) comprises pressure lysis.

13. The method of claim 12, wherein the pressure lysis utilizes a microfluidiser.

14. A method comprising:
a) lysing adenovirus-infected cells to generate a whole-cell lysate comprising active adenovirus, wherein said lysing comprises a combination of detergent and pressure lysis;
b) applying said lysate to at least one chromatographic matrix; and
c) recovering a composition of adenovirus particles with 60-100% of the adenoviral activity of the whole cell lysate.

15. A method comprising:
a) lysing adenovirus-infected cells to generate a whole-cell lysate comprising active adenovirus, wherein said lysing does not involve repeated freeze-thawing;
b) applying said lysate to a first chromatographic matrix;
c) applying the eluate from the chromatographic matrix to a second chromatographic matrix; and
d) recovering a composition of adenovirus particles with at least 50% of the adenoviral activity of the whole cell lysate.

16. The method of claim 15, wherein step (a) comprises detergent lysis.

17. The method of claim 16, wherein the detergent is Tween-80.

18. A method comprising:
a) lysing adenovirus-infected cells to generate a whole-cell lysate comprising active adenovirus
b) applying said lysate to a first chromatographic matrix;
c) applying the eluate from the chromatographic matrix to a second chromatographic matrix; and
d) recovering a composition of adenovirus particles with at least 50% of the adenoviral activity of the whole cell lysate, wherein at least about a milligram of active adenovirus particles are recovered.

19. The method of claim 18, wherein step (a) comprises detergent lysis.

20. The method of claim 19, wherein the detergent is Tween-80.

21. A method comprising,
a) lysing adenovirus-infected cells to generate a whole-cell lysate comprising active adenovirus, wherein said lysing does not involve repeated freeze-thawing and wherein said lysing comprises a combination of detergent and pressure lysis;
b) applying said lysate to at least one chromatographic matrix; and
c) recovering a composition of adenovirus particles with 60-100% of the adenoviral activity of the whole cell lysate.

22. A method comprising:
a) lysing adenovirus-infected cells to generate a whole-cell lysate comprising active adenovirus, wherein said lysing comprises a combination of detergent and pressure lysis;
b) applying said lysate to at least one chromatographic matrix; and
c) recovering a composition of adenovirus particles with 60-100% of the adenoviral activity of the whole cell lysate, wherein at least about a milligram of active adenovirus particles are recovered.

* * * * *